United States Patent
Scott et al.

(10) Patent No.: US 10,556,089 B2
(45) Date of Patent: **\*Feb. 11, 2020**

(54) FLEX CIRCUIT RIBBON BASED ELONGATED MEMBERS AND ATTACHMENTS

(71) Applicant: Heraeus Medical Components LLC, St. Paul, MN (US)

(72) Inventors: Steven E. Scott, Excelsior, MN (US); Jahn Stopperan, Lakeville, MN (US); John Tracy, Northfield, MN (US); Greg Closser, Northfield, MN (US)

(73) Assignee: Heraeus Medical Components LLC, St. Paul, MN (US)

( * ) Notice: Subject to any disclaimer, the term of this patent is extended or adjusted under 35 U.S.C. 154(b) by 116 days.

This patent is subject to a terminal disclaimer.

(21) Appl. No.: 15/895,585

(22) Filed: Feb. 13, 2018

(65) Prior Publication Data

US 2018/0193594 A1     Jul. 12, 2018

Related U.S. Application Data

(63) Continuation of application No. 14/436,416, filed as application No. PCT/US2013/066318 on Oct. 23, 2013, now Pat. No. 9,925,354.

(Continued)

(51) Int. Cl.
    *A61M 25/00*     (2006.01)
    *A61B 5/04*     (2006.01)
    (Continued)

(52) U.S. Cl.
    CPC ........... *A61M 25/0045* (2013.01); *A61B 5/04* (2013.01); *A61B 5/0538* (2013.01);
    (Continued)

(58) Field of Classification Search
    CPC .......... A61M 25/0045; A61M 25/0009; A61M 25/0012; A61M 2205/0233;
    (Continued)

(56) References Cited

U.S. PATENT DOCUMENTS 4,014,343 A    3/1977 Esty
4,484,586 A    11/1984 McMickle et al.
(Continued)

FOREIGN PATENT DOCUMENTS

WO    WO-2011005165 A1    1/2011
WO    WO-2011031201 A1    3/2011
WO    WO-2014066470 A1    5/2014

OTHER PUBLICATIONS

"U.S. Appl. No. 14/436,416, Examiner Interview Summary dated Oct. 10, 2017", 3 pgs.

(Continued)

*Primary Examiner* — Mallika D Fairchild
(74) *Attorney, Agent, or Firm* — Dicke, Billig & Czaja, PLLC

(57) ABSTRACT

A catheter or other elongated member can include an elongated inner portion, an elongated outer portion, a flex circuit ribbon comprising at least one conductor, and an electrical contact. The flex circuit ribbon can be situated between the inner portion and the outer portion. The inner portion and the outer portion can be (1) affixed together between portions of the flex circuit ribbon or (2) integrally formed such that masses of the inner and outer portions are joined together between portions of the flex circuit ribbon. The electrical contact can be configured to be exposed during use. The electrical contact can be situated at, or connected to, the at least one conductor of the flex circuit ribbon.

20 Claims, 13 Drawing Sheets

Related U.S. Application Data

(60) Provisional application No. 61/717,735, filed on Oct. 24, 2012.

(51) Int. Cl.
*A61B 5/00* (2006.01)
*A61B 5/053* (2006.01)
*H01B 7/04* (2006.01)
*H01B 7/08* (2006.01)
*H01B 13/34* (2006.01)
*A61B 18/14* (2006.01)

(52) U.S. Cl.
CPC ....... *A61B 5/6852* (2013.01); *A61M 25/0009* (2013.01); *H01B 7/04* (2013.01); *H01B 7/08* (2013.01); *H01B 13/34* (2013.01); *A61B 18/1492* (2013.01); *A61M 25/0012* (2013.01); *A61M 2205/0233* (2013.01); *A61M 2207/00* (2013.01); *Y10T 29/49147* (2015.01)

(58) Field of Classification Search
CPC ............. A61M 2207/00; A61B 5/0538; A61B 5/6852; A61B 5/04; A61B 18/1492; H01B 13/34; H01B 7/08; H01B 7/04; Y10T 29/49147
See application file for complete search history.

(56) References Cited

U.S. PATENT DOCUMENTS

| | | | |
|---|---|---|---|
| 4,981,478 | A | 1/1991 | Evard |
| 5,057,092 | A | 10/1991 | Webster |
| 5,417,208 | A | 5/1995 | Winkler |
| 5,951,539 | A | 9/1999 | Nita et al. |
| 7,322,988 | B2 | 1/2008 | Sterud et al. |
| 7,762,954 | B2 | 7/2010 | Nix et al. |
| 8,285,362 | B2 | 10/2012 | Dietz et al. |
| 2002/0103445 | A1 | 8/2002 | Rahdert et al. |
| 2004/0031619 | A1 | 2/2004 | Lettmann et al. |
| 2004/0054289 | A1 | 3/2004 | Eberle et al. |
| 2006/0100618 | A1 | 5/2006 | Chan et al. |
| 2008/0288036 | A1 | 11/2008 | Greenberg et al. |
| 2009/0088631 | A1 | 4/2009 | Dietz et al. |
| 2010/0305420 | A1 | 12/2010 | Curry |
| 2012/0078077 | A1 | 3/2012 | Harley et al. |
| 2012/0172696 | A1 | 7/2012 | Kallback et al. |
| 2015/0273184 | A1 | 10/2015 | Scott et al. |

OTHER PUBLICATIONS

"U.S. Appl. No. 14/436,416, Non Final Office Action dated Jun. 19, 2017", 14 pgs.

"U.S. Appl. No. 14/436,416, Notice of Allowance dated Nov. 17, 2017", 5 pgs.

"U.S. Appl. No. 14/436,416, Response filed Oct. 16, 2017 to Non Final Office Action dated Jun. 19, 2017", 14 pgs.

"International Application Serial No. PCT/US2013/066318, International Preliminary Report on Patentability dated May 7, 2015", 9 pgs.

"International Application Serial No. PCT/US2013/066318, International Search Report dated Mar. 21, 2014", 2 pgs.

"International Application Serial No. PCT/US2013/066318, Written Opinion dated Mar. 21, 2014", 7 pgs.

"Nano Plastic Circular Connectors—Type WC—Accessories/HW", [Online]. Retrieved from the Internet. <http://www.omnetics.com/products/circular-nano_plastic-WC>, (Accessed Jun. 22, 2012), 2 pgs.

"Nano Plastic Circular Connectors—Type WC—Data Sheet MIL-DTL-32139", [Online]. Retrieved from the Internet. <http://www.omnetics.com/products/circular-nano_plastic-WC>, (Accessed Jun. 22, 2012), 1 pg.

"Nano Plastic Circular Connectors—Type WC Ordering Guide", [Online]. Retrieved from the Internet. <http://www.omnetics.com/products/circular-nano_plastic-WC>, (Accessed Jun. 22, 2012), 1 pg.

"Nano Plastic Circular Connectors—Type WC Specifications", [Online]. Retreived from the Internet <http://www.omnetics.com/products/circular-nano_plastic-WC>, (Accessed Jun. 22, 2012), 2 pgs.

"Nanp Plastic Circular Connectors—Type WC—Pin/Socket", [Online]. Retrieved from the Internet. <http://www.omnetics.com/products/circular-nano_plastic-WC>, (Accessed Jun. 22, 2012), 2 pgs.

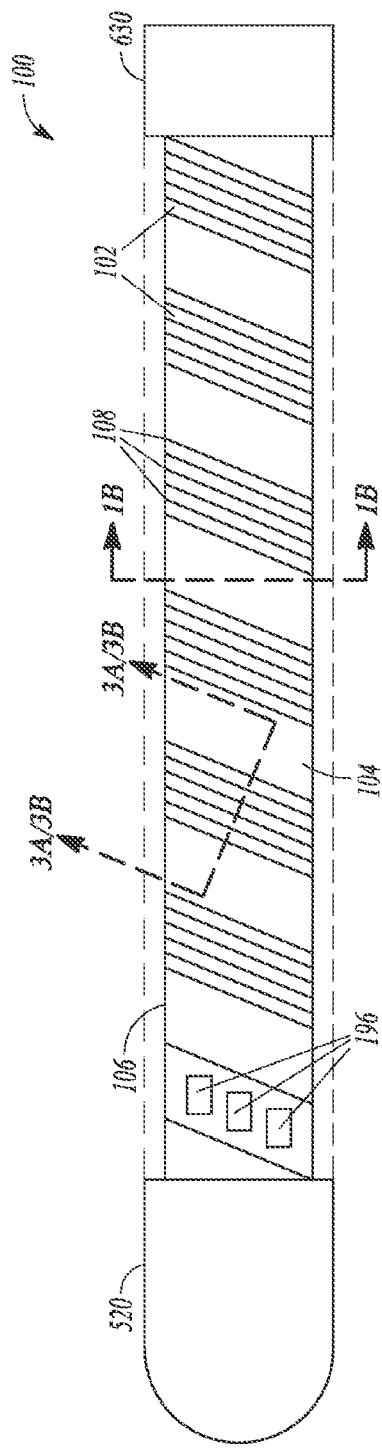
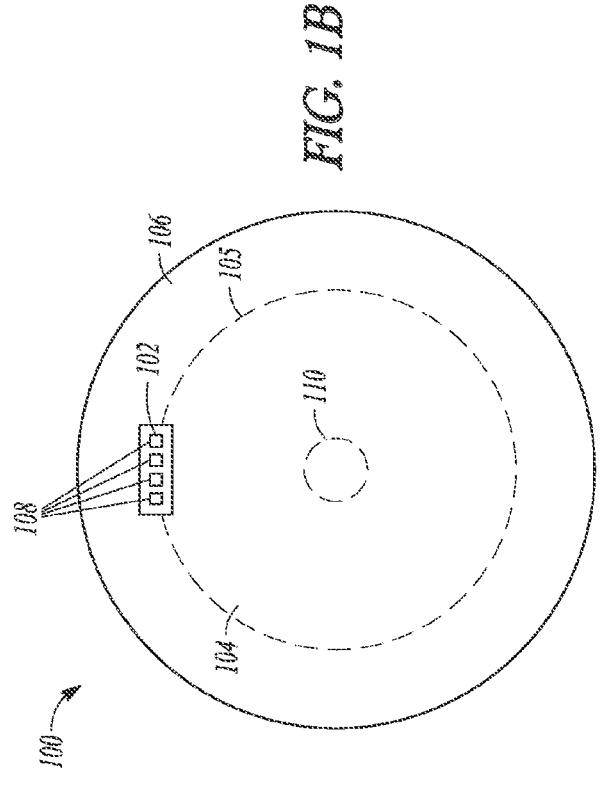
FIG. 1A
FIG. 1B

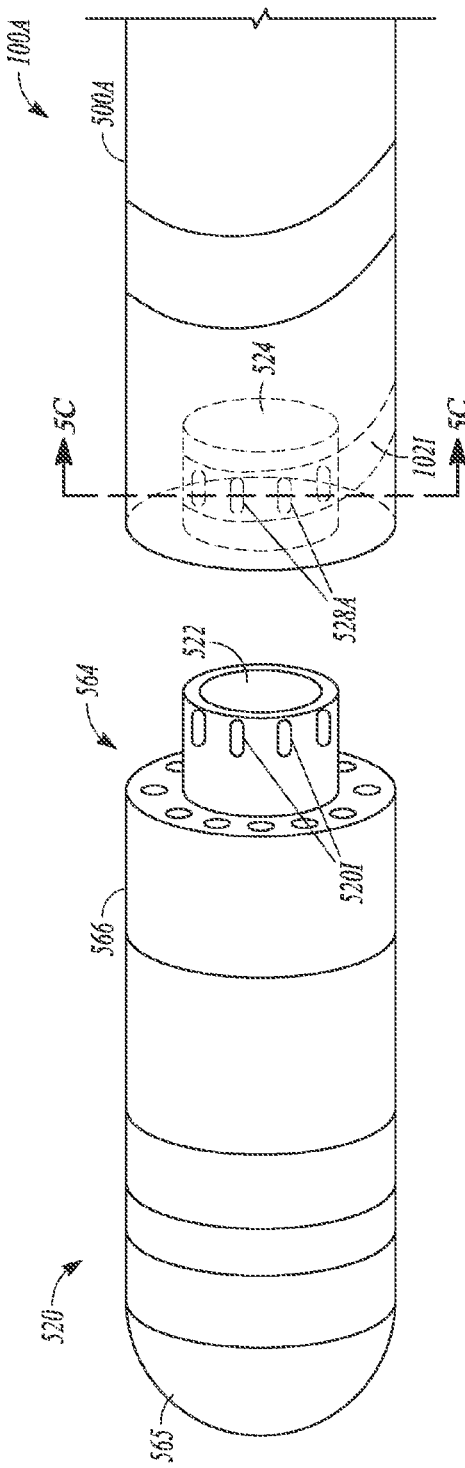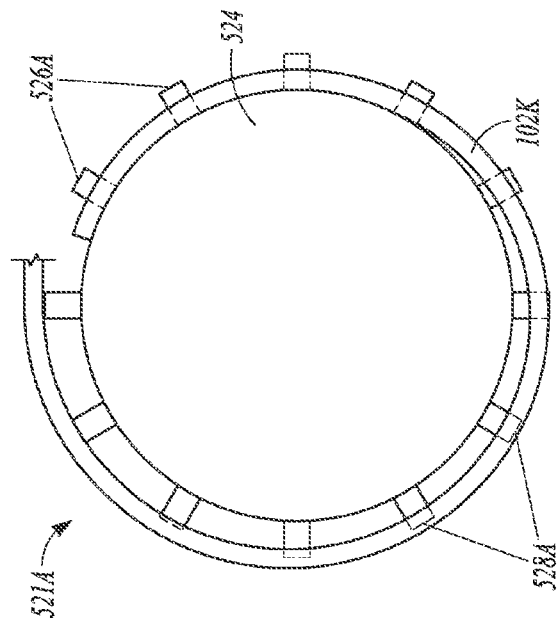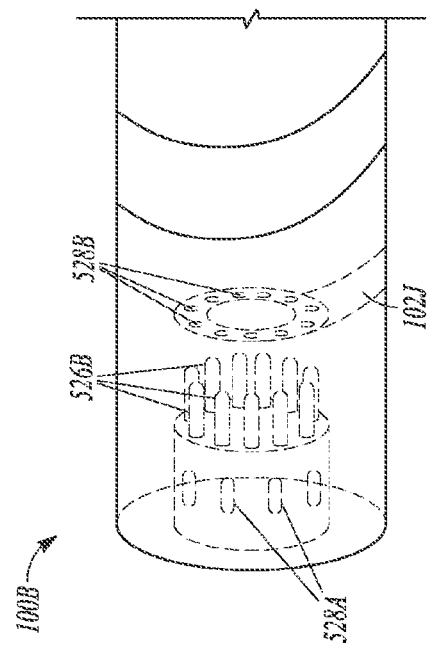

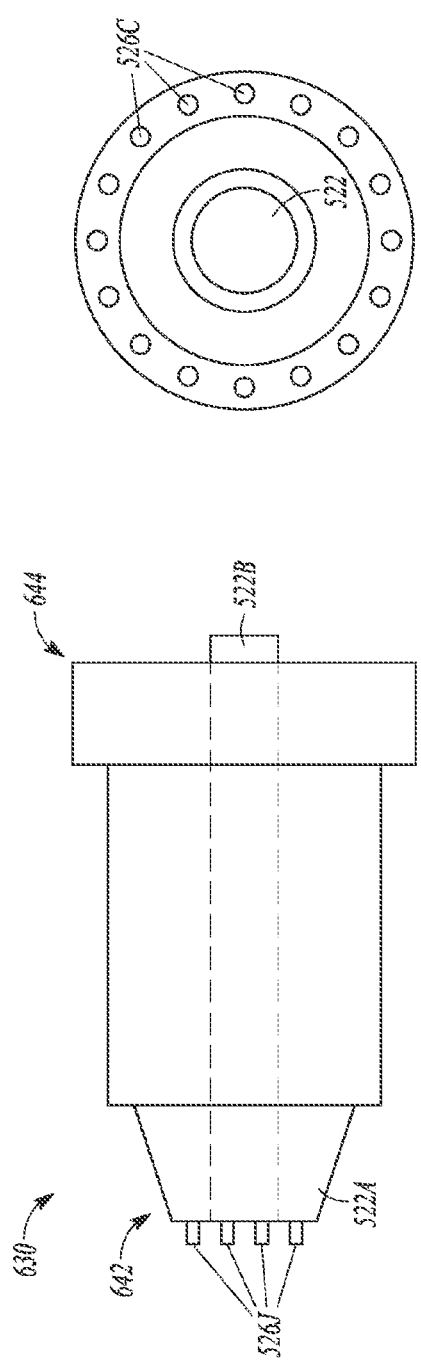
FIG. 6A
FIG. 6C
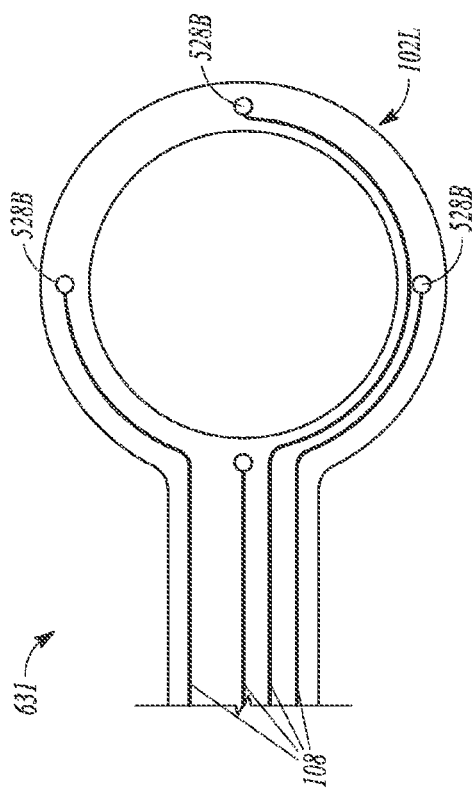
FIG. 6B

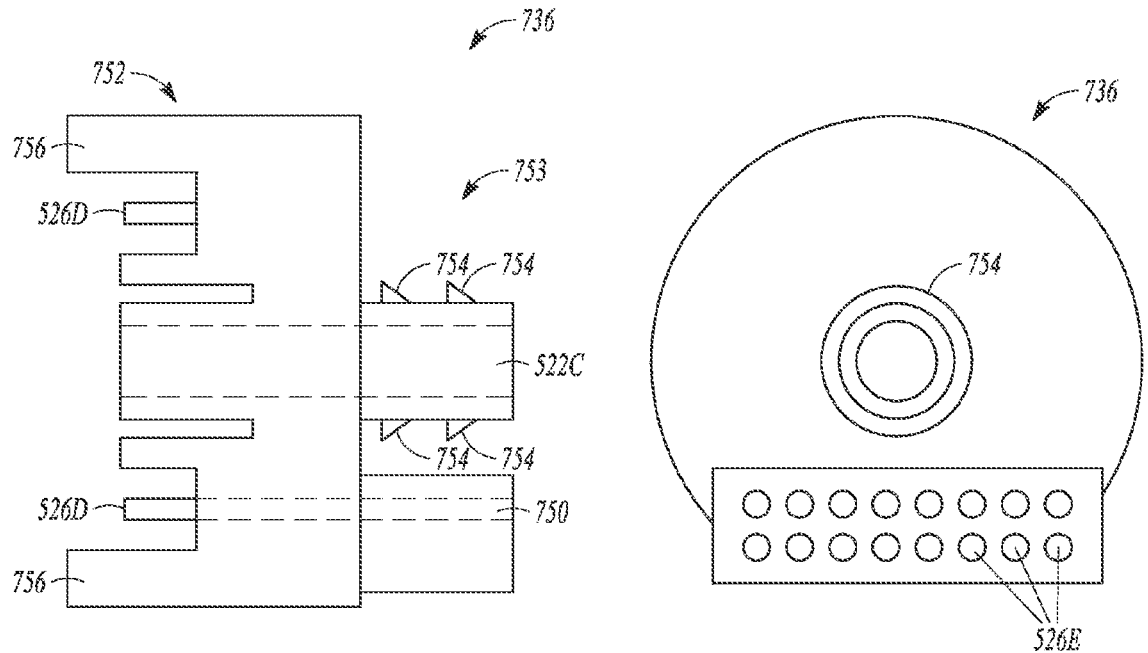
*FIG. 7A*  *FIG. 7B*
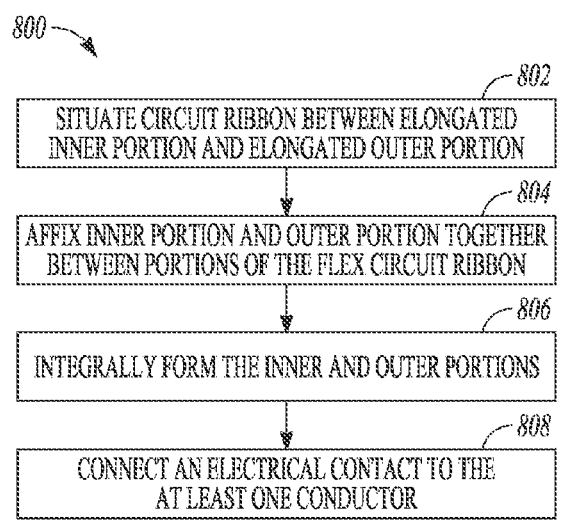
*FIG. 8*

FLEX CIRCUIT RIBBON BASED ELONGATED MEMBERS AND ATTACHMENTS

CLAIM OF PRIORITY

This application is a continuation of U.S. application Ser. No. 14/436,416, filed Apr. 16, 2015, which claims the benefit of priority U.S. National Stage Filing under 35 U.S.C. 371 from International Application No. PCT/US2013/066318, filed on Oct. 23, 2013, and published as WO 2014/066470 A1 on May 1, 2014, which claims the benefit of priority of U.S. Provisional Patent Application Ser. No. 61/717,735, filed on Oct. 24, 2012, all of which are herein incorporated by reference in their entireties.

BACKGROUND

U.S. Pat. No. 7,762,954, issued on Jul. 27, 2010, is directed to an ultrasonic imaging catheter that is provided with a flexible circuit electrically coupled to a transducer array mounted on the distal end of the catheter, a portion of the flexible circuit being helically wound about the catheter in order to enhance the flexibility of the circuit. The catheter can be a balloon catheter which is also provided with a stent mounted on the balloon, the stent carrying one or more drugs designed to be eluted or washed into a patient's blood stream after the stent has been delivered, by the balloon catheter, into a target area within the patient's vascular system.

OVERVIEW

The present inventors have recognized, among other things, that a problem to be solved can include reducing the labor in manufacturing a catheter or other electrically conductive elongated member. The present subject matter can help address this, such as by replacing individual wires of an elongated member with a flex circuit ribbon, thus reducing the number of wires to be individually coupled.

Another problem can include obtaining a specific desired mechanical stiffness or torque response characteristic. This can be addressed by embedding a flex circuit ribbon in the elongated member, such as in a wall structure of the elongated member. A specific amount of a stiffener can be situated on a surface of the flex circuit ribbon to establish a desired mechanical stiffness or torque response characteristic of that portion of the elongated member.

Another problem can include providing electrical energy at a specific location external to a catheter or other electrically conductive elongated member. This can be addressed by embedding a helically wound flex circuit ribbon in the elongated member. This can provide easier access to conductors within the elongated member.

Another problem can include providing an electrically conductive elongated member with a desired specified electric field distribution or current density. This can be addressed using a helically wound flex circuit ribbon embedded in the elongated member or by terminating a pattern of electrodes on or near the outside surface of the catheter. By selecting the number of times the flex circuit ribbon is wound within the elongated member, the spacing of the windings, or both, the electric field, current density, or both, of the elongated member can be altered.

Another problem can include providing an electrically conductive elongated member with mounting pads on an exposed, inner surface of a catheter. Such mounting pads can be used for the placement of sensors, electrodes, or other electric or electronic components.

Another problem can include the diameter of the elongated member limiting the number of independent conductive elements that can be situated within or connected to. Such a limitation can reduce the number of electrical signals that can be transmitted at or near an end of an elongated member, such as the distal end.

Another problem can include creating a connector operable to connect to a catheter or other electrically conductive elongated tubular member, such as can provide both electrical conductivity and access of a lumen of the catheter or other tubular member, such as simultaneously. It can be desired to connect to twenty or more conductors within such dimensions. This can be addressed by providing a connector configured to segregate electrical conductivity and access to a lumen of a catheter or other electrically conductive elongated tubular member.

This document discloses, among other things, a catheter or other elongated member can include an elongated inner portion, an elongated outer portion, a flex circuit ribbon comprising at least one conductor, and an electrical contact. The flex circuit ribbon can be situated between the inner portion and the outer portion. The inner portion and the outer portion can be (1) affixed together between portions of the flex circuit ribbon or (2) integrally formed such that masses of the inner and outer portions are joined together between portions of the flex circuit ribbon. The electrical contact can be configured to be exposed during use. The electrical contact can be situated at, or connected to, the at least one conductor of the flex circuit ribbon.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals can describe similar components in different views. Like numerals having different letter suffixes can represent different instances of similar components. The drawings illustrate generally, by way of example, but not by way of limitation, various embodiments discussed in the present document.

FIG. 1A illustrates a side view of an example of an apparatus.

FIG. 1B illustrates a cross-section view of an example of an apparatus.

FIG. 5A illustrates a side view of an example of an elongated member.

FIG. 5B illustrates a side view of an example of a connector portion of an elongated member.

FIG. 5C illustrates a cross-section view of an example of a connector portion of an elongated member.

FIG. 6A illustrates a side view of an example of a connector.

FIG. 6B illustrates an end view of an example of a connector.

FIG. 6C illustrates an example of a portion of a flex circuit ribbon.

FIG. 7A illustrates a side view of an example of an interface connector.

FIG. 7B illustrates an end view of an example of an interface connector.

FIG. 8 illustrates an example of a technique of making an elongated member.

DETAILED DESCRIPTION

Figure 1C:
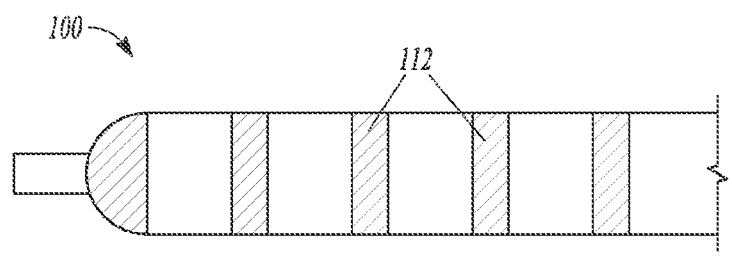
FIG. 1C illustrates a side view of an example of an apparatus.

This document describes, among other things, a catheter or other elongated member that can include an elongated inner portion, an elongated outer portion, a flex circuit ribbon comprising at least one conductor, and an electrical contact. The flex circuit ribbon can be situated between the inner portion and the outer portion. The inner portion and the outer portion can be (1) affixed together between portions of the flex circuit ribbon or (2) integrally formed such that masses of the inner and outer portions are joined together between portions of the flex circuit ribbon. The electrical contact can be configured to be exposed during use. The electrical contact can be situated at, or connected to, the at least one conductor of the flex circuit ribbon. Other aspects and details are explained herein.

FIGS. 1A-1D show various views of an example of a catheter or other elongated member 100. The elongated member 100 can include a flex circuit ribbon 102, an elongated inner portion 104, and an elongated outer portion 106. The elongated member 100 can optionally include a lumen 110. The lumen 110 can extend within the inner portion 104, such as longitudinally along a central axis of the elongated member 100.

The flex circuit ribbon 102 can be situated between the inner portion 104 and the outer portion 106, such as helically at a boundary 105 therebetween. Such a helical winding can include the flex circuit ribbon 102 covering about half of the inner surface of the outer portion (e.g., the flex circuit ribbon 102 can be helically situated with a gap about the size of the width of the flex circuit ribbon 102 between windings of the flex circuit ribbon 102). Such a configuration can provide sufficient area between windings of the flex circuit ribbon 102 so as to allow the inner portion and the outer portion to be sufficiently joined or fused together between the windings. Providing a sufficient number of windings and gaps between windings can help prevent creating voids around the flex circuit ribbon 102 after the inner portion and outer portion have been joined or fused with the flex circuit ribbon situated therebetween. The flex circuit ribbon 102 can be situated about or outside the lumen 110.

Figure 1D:
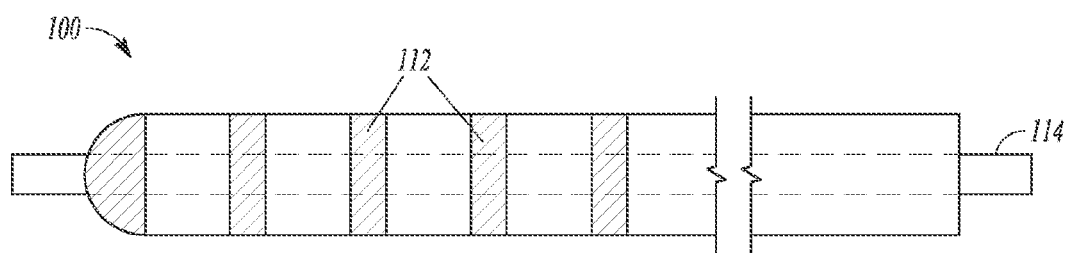
FIG. 1D illustrates a side view of an example of an apparatus.

The flex circuit ribbon 102 can include one or more conductor(s) 108. The conductors 108 can be embedded within a flexible insulator of the flex circuit ribbon 102, such as described and explained herein. The conductors 108 can be respectively electrically coupled to one or more electrical contact(s) 112, such as shown in FIG. 1D, such as described and explained herein.

The inner portion 104 and the outer portion 106 can be separately formed, then affixed together, such as between (e.g., helically wound) portions of the flex circuit ribbon 102. The separately formed inner portion 104 and outer portion 106 can respectively include an elongated inner member, including an outer surface 105, such as at or near the boundary indicated by the dashed line, and an elongated tubular outer member, including an inner surface, such as at or near the boundary indicated by the dashed line.

The inner portion 104 and the outer portion 106 can be integrally formed, such as with the outer surface 105 of the inner portion 104 conceptually defined, at least partially, by the flex circuit ribbon 102. The inner portion 104 and the outer portion 106 can include masses, such that masses of the inner portion 104 and outer portion 106 can be joined together between portions of the flex circuit ribbon. Such a joining of the masses can occur at or around the time the inner portion 104 and the outer portion 106 are integrally formed. Integrally forming the inner portion 104 and the outer portion 106 can include using a process such as injection molding or three dimensional (3D) printing.

The optional lumen 110 can be configured to allow one or more of a solid (e.g., a guidewire) or a flowable material (e.g., a liquid, a gas, or a gel) to pass therethrough. The lumen 110 can be configured to be pneumatic, such as to communicate or transport pressurized air or a vacuum. The lumen 110 can be configured to be hydraulic, such as to communicate or transport a pressurized or unpressurized liquid. The lumen 110 can be connected or otherwise configured as a drug or other therapeutic agent delivery lumen. The lumen 110 can be configured as a mechanical access lumen, such as to permit physical insertion or withdrawal of one or more instruments or one or more other solid materials therein.

The electrical contact 112 can include one or more electrodes. The electrode or other electrical contact 112 can be configured to be exposed during use, such as to directly contact tissue or one or more objects external to the elongated member 100 while the elongated member 100 is in use. The electrical contact 112 may be on or near the outside surface 568 (see FIG. 5A) of the elongated member 100.

Figure 2:
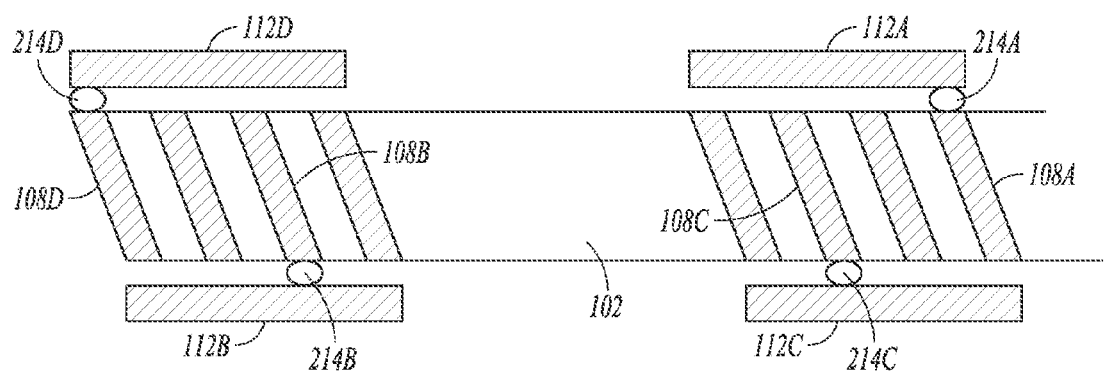
FIG. 2 illustrates an example of a coupling between an electrical contact and a conductor of a flex circuit ribbon.
Figure 3A:
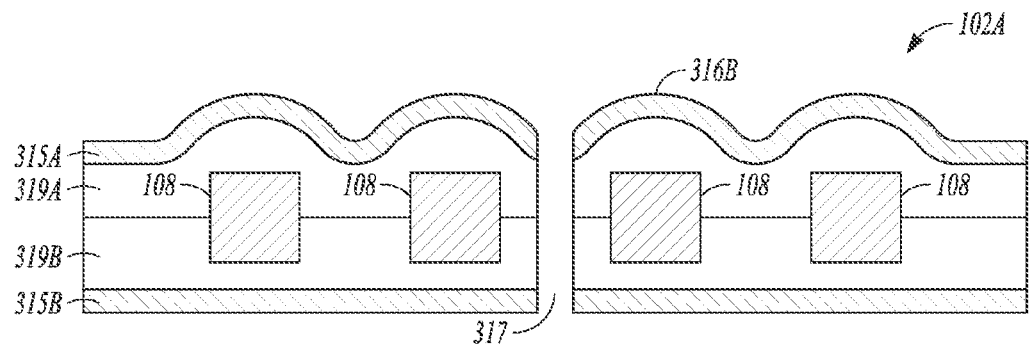
FIGS. 3A-3B illustrate a cross-section view of and example of a flex circuit ribbons.
Figure 3B:
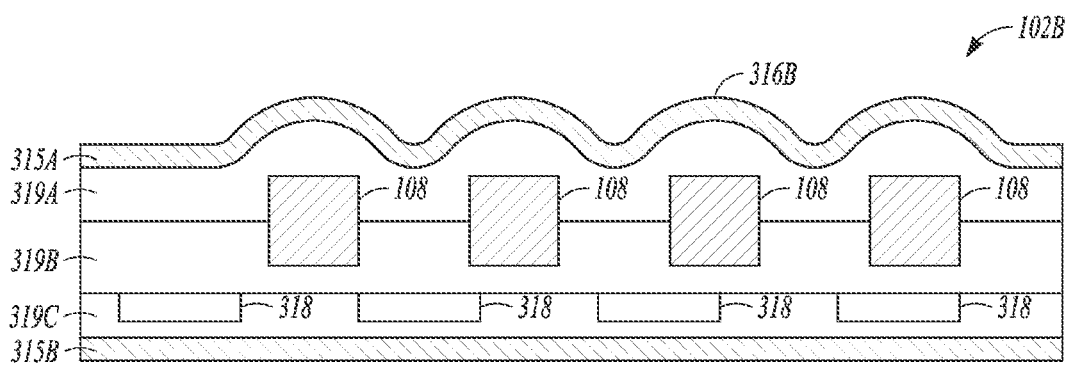

FIG. 2 illustrates an example of the flex circuit ribbon 102, in which a plurality of electrical contacts 112A-D can be respectively individually electrically coupled to a plurality of conductors 108A-D. Such respective individual electrical coupling can be made by individually selectively exposing a conductor 108A-D, such as by selectively removing a portion of a flexible insulator covering the conductor 108A-D, such as a flexible polymer layer 315 or an adhesive layer 319 (such as depicted in FIGS. 3A-B), of the flex circuit ribbon 102, and attaching an intermediate material 214A-D to the exposed conductor 108A-D. Examples of suitable intermediate materials 214 can include Indium Solder or Elektriska Svetsnings Aktiebolaget (ESAB) brazing alloy.

Selectively removing the portion of the flexible insulator can include using mechanical abrasion or laser ablation to expose the conductor 108, or the flex circuit ribbon 102 can be manufactured such that the conductor 108 is exposed, such as to obviate or bypass the need to expose the conductors 108. This can avoid any need for exposing the conductor 108 after manufacture of the flex circuit ribbon 102. The flex circuit ribbon 102 can include an adhesive or other intermediate material 214, such as can be connected to the conductor 108A-D of the flex circuit ribbon 102 at the exposed portion of the conductor 108A-D. An electrode or other electrical contact 112 can be welded or adhered to the intermediate material 214, such as using a conductive epoxy, such as Hysol® Eccobond™ conductive adhesive.

A heat shrink or other tubing can be placed around the assembly of the flex circuit ribbon 102 and the electrical contact 112. The heat shrink tubing can be heated, such as to respectively individually electrically connect the conductor 108A-D of the flex circuit ribbon 102 to a respective electrode or other electrical contact 112A-D. The heat shrink tubing can be selectively removed to expose the electrical contacts 112, such as by selectively grinding, laser ablation, or other removal processes.

FIG. 3A illustrates a cross-sectional view of an example of the flex circuit ribbon 102. The flex circuit ribbon 102 can include one or more conductors 108 that can be embedded, at least partially, between a first surface 316A and a second surface 316B of the flex circuit ribbon 102. The flex circuit ribbon 102 can include a hole 317 therethrough. The hole 317 can allow for a mechanical or electrical connection between the inner portion 104 and the outer portion 106, between which the flex circuit ribbon 102A can be situated. The hole 317 can provide increased contact area between the inner portion 104 and the outer portion 106, between which the flex circuit ribbon 102A can be situated.

The flex circuit ribbon 102 can include a flexible polymer layer 315A-B. Examples of materials that can be used to make the flexible polymer layer 315A-B can include polyester, polyimide, polyethylene napthalate, poly etherimide, fluoropolymer, or one or more other flexible polymers. The flexible polymer layer 315 can be an about 0.001 inch (0.0254 mm) thick layer of Kapton, a tradename of Dupont Corporation. The flexible polymer layer 315A can be bonded to another flexible polymer layer 315B, such as by at least one adhesive layer 319A-B. The adhesive layer 319A-B can include an acrylic thermoset adhesive. The adhesive layer 319A-B can include an about 0.001 inch (0.0254 mm) thick layer of Pyralux®, a tradename of Dupont Corporation.

The conductors 108 can be made by forming, placing, or otherwise situating a layer of conductor material on the adhesive layer 319 and etching the layer of conductor material to shape the conductor material into the conductors 108. The conductors 108 can include various shapes or thicknesses. The conductor 108, or the layer of conductor material from which it is formed, can include about half-ounce rolled annealed copper that can be about 0.0007 inches (0.01778 mm) thick or thicker, such as about 0.0028 inches (0.07112 mm) or about 0.0035 inches (0.0889 mm) thick. Adjacent conductors 108 can be separated by about 0.002 to 0.005 inches (0.0508 to 0.127 mm). The conductors 108 can be mostly straight with few curves.

The flex circuit ribbon 102 can include one or more conductors 108 that can be embedded in a single flexible polymer layer 315. The flex circuit ribbon 102 can include conductors 108 that can be situated between multiple flexible polymer layers 315 that can be bonded together, such as at adjacent portions of the flexible polymer layers 315. Multiple layers of conductors 108 can be situated within the flex circuit ribbon 102, such as two or more layers of conductors 108 separated by one or more flexible polymer layers 315 (e.g., insulating layers) or one or more adhesive layers 319.

A flex circuit ribbon 102B can include a stiffener 318, such as can be disposed on one or both surfaces 316A-B of the flex circuit ribbon 102B. In the example of FIG. 3B, the flex circuit ribbon 102B can include five layers. The flex circuit ribbon 102B can include at least one flexible polymer layer 315A-B. The flex circuit ribbon 102B can include a flexible polymer layer 315A that can be bonded to another flexible polymer layer 315B, such as by at least one adhesive layer 319A-C.

The stiffener 318 can be situated on a surface 316 of the flex circuit ribbon 102. A layer of stiffener material can be formed, placed, or otherwise situated on the adhesive layer 319A-C. The layer of stiffener material can be shaped, such as by etching, to pattern or otherwise selectively define the stiffener 318. The stiffener 318 can be situated on a surface of the flex circuit ribbon 102 without etching, such as by selectively forming the stiffener 318 in a desired pattern. The stiffener 318 can include various shapes and thicknesses, such as shown in FIGS. 4A-E.

Figure 3C:
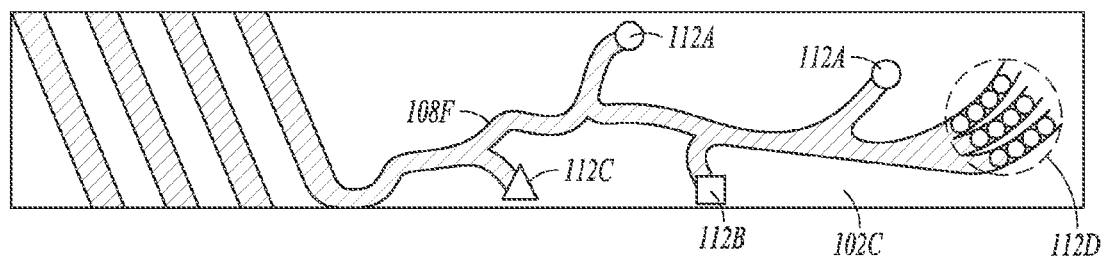
FIG. 3C illustrates a planar view of an example of a flex circuit ribbon.

FIG. 3C is a cross-section view of an example of a flex circuit ribbon 102C. The flex circuit ribbon 102C can include a plurality of individual electrodes or other electrical contacts 112A-C, such as an electrical contact array 112D. The flex circuit ribbon manufacturing allows the flex circuit ribbon 102 to include a variety of conductor 108 or electrical contact 112 shapes, sizes, or arrays, such as shown in FIG. 3C. The electrical contact array 112D can include a plurality of individual electrical contacts 112, such as can be programmably or permanently configured to effectively form a single electrode or other electrical contact 112. The at least one conductor 108 can be situated in various locations on, or at least partially in, the flex circuit ribbon 102. The electrical contact 112 can be electrically coupled to one or more conductors 108 of the flex circuit ribbon 102 in one or more locations.

By establishing or varying the distribution of electrical contacts 112 or conductors 108, the electric field created by the elongated member 100 or the current density within a conductive portion (e.g., conductor 108, electrical contact 112, etc., or a combination thereof) of the elongated member 100 can be specified or altered. The electric field or current density can be specified or altered to provide a desired electric field distribution or a desired current density distribution of the elongated member 100.

The resistivity of the flex circuit ribbon 102 can be specified or altered, such as by choosing or altering the conductor material, or a thickness or a shape of the conductors 108. When the elongated member 100 is to be used for sensing an intrinsic or other electrical signal, such as a cardiac or neurological signal, the flex circuit ribbon 102 can be configured with a resistivity of about 100 Ohms. If the elongated member 100 is to be used for tissue ablation or tissue electro-stimulation, the flex circuit ribbon 102 can be configured with a resistivity of about 5 Ohms.

FIGS. 4A-E show examples of flex circuit ribbons 102D-H that can include a stiffener 318A-E that can be selectively formed, placed, or otherwise situated on, or at least partially in, the corresponding flex circuit ribbon 102D-H. A surface 316A-E of the flex circuit ribbon 102D-H can include the stiffener 318A-E selectively formed, selectively patterned, or otherwise selectively situated thereon. The stiffener 318A-E can include an electrically conductive material, such as a metal, such as stainless steel, copper, aluminum, Cupernickel, nitinol, Inconel®, or a combination thereof. The stiffener 318A-E can be selectively situated on a surface 316A-E of the flex circuit ribbon 102D-H, such as to provide at least one of a specified stiffener coverage (e.g., areal coverage) of the surface 316A-E of the flex circuit ribbon 102D-H; a specified stiffener pattern on at least a portion of the surface 316A-E of the flex circuit ribbon 102D-H; a specified mechanical torque response characteristic of at least a portion of the associated elongated member 100; or a specified mechanical stiffness characteristic of at least a portion of the associated elongated member 100. The stiffener 318A-E can be formed, placed, or otherwise situated on the surface 316A-E of the flex circuit ribbon 102D-H to provide the specified stiffener pattern, the specified mechanical torque response characteristic, or the specified mechanical stiffness characteristic of at least a portion of an elongated member 100 that includes the flex circuit ribbon 102D-H. The stiffener 318A-E can be selectively formed or patterned to permit including different stroke width, spacing, or pitch of the stiffener 318A-E, e.g., so that varying amounts of stiffener 318A-E remain on the surface 316A-E. The stiffener 318A-E can include varying thickness such as to vary the height of the stiffener 318A-E from the surface 316A-E.

Figure 4A:
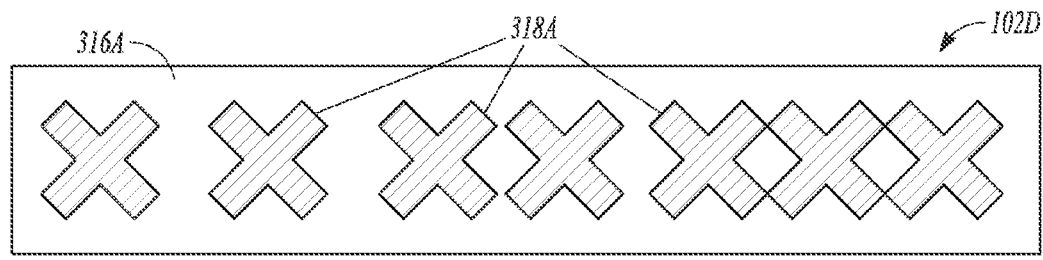
FIGS. 4A-4E illustrate a planar view of an example of a flex circuit ribbon.
Figure 4B:
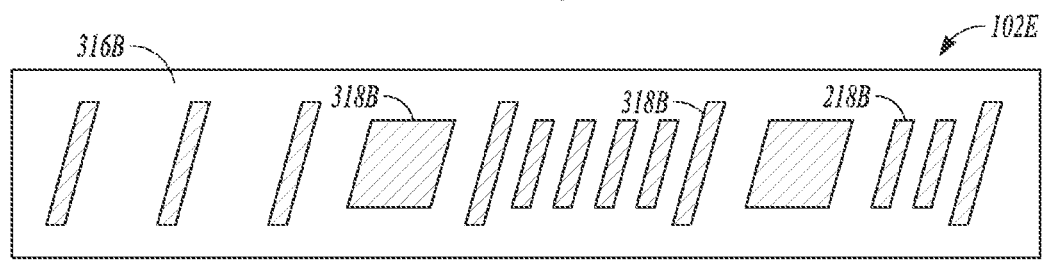
Figure 4C:
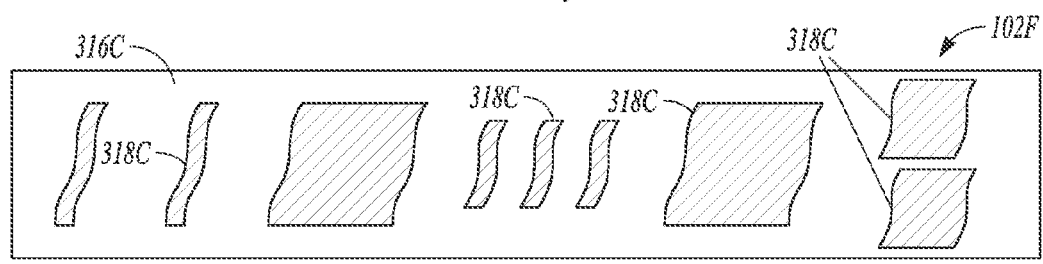
Figure 4D:
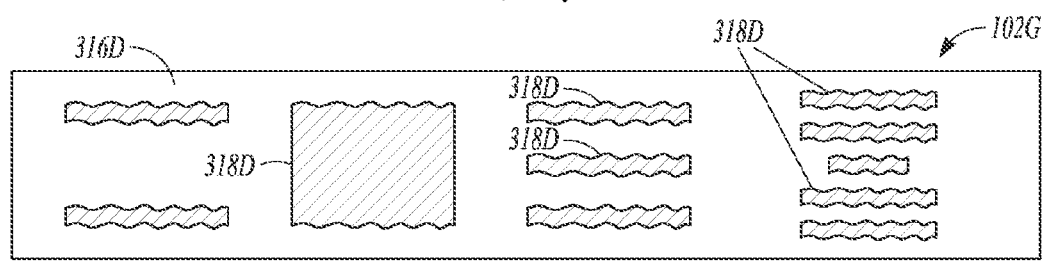
Figure 4E:
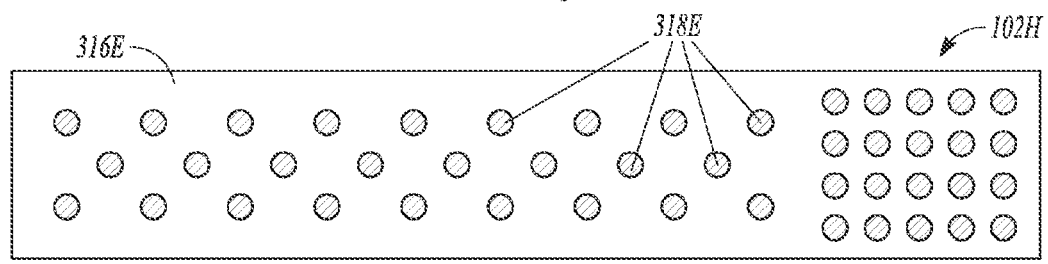

Illustrative examples of stiffener patterns can include one or any combination of: cross-hatches or "X" patterns, such as shown in FIG. 4A, slashes, such as shown in FIG. 4B, "S" or "Z" patterns, such as shown in FIG. 4C, "wiggles," such as shown in FIG. 4D, dot patterns, such as shown in FIG. 4E, or one or more other patterns or configurations. The stiffener 318A-E can serve as an electrical connection or as electrical shielding for the catheter or other elongated member 100.

By selectively situating or patterning stiffener 318 on a portion of the surface 316 of the flex circuit ribbon 102 a mechanical torque response characteristic (e.g., an amount of torque produced by the elongated member 100 when an external force is applied thereto) or mechanical stiffness characteristic of an elongated member 100 can be specified or altered. Since the inner portion 104 and outer portion 106 of the elongated member 100 can be at least partially adjacent or contiguous with a surface 316 of the flex circuit ribbon 102, the mechanical stiffness or mechanical torque response characteristic of the elongated member 100 can be proportional to the mechanical stiffness or torque response characteristic of the flex circuit ribbon 102. Increasing the mechanical stiffness or torque response of a portion of the flex circuit ribbon 102, such as by covering more of the surface 316 of the flex circuit ribbon 102 with the stiffener 318, can increase the mechanical stiffness or torque response characteristic of that portion of the flex circuit ribbon 102 and the corresponding mechanically coupled portion of the elongated member 100. Also, decreasing the amount of stiffener coverage of a portion of a surface of the flex circuit ribbon can decrease the mechanical stiffness or torque response characteristic of a portion of the flex circuit ribbon 102 and a corresponding mechanically coupled portion of the elongated member 100.

Including a shape-memory stiffener, such as nitinol, on a surface 316 of the flex circuit ribbon 102 can provide an elongated member 100 of which at least a portion can have shape memory. This can allow the shape of a portion of the elongated member to be altered, and the portion of the elongated member 100 that includes the shape-memory stiffener can be heated to a sufficient temperature to return that portion of the elongated member 100 to substantially the same shape it was before it was altered.

The stiffener 318 can be selectively formed, placed, or otherwise situated on the surface 316 of the flex circuit ribbon 102 such that a greater quantity of the stiffener 318 can be situated on a first portion of the surface 316 of the flex circuit ribbon 102 than on a second portion of the surface of the flex circuit ribbon 102, such as shown in FIG. 4A. The first portion of the surface 316 of the flex circuit ribbon 102 can be longitudinally situated differently than the second portion of the surface 316 of the flex circuit ribbon 102, such as shown in FIG. 4A. For example, the first portion of the surface 316 of the flex circuit ribbon 102 can be situated more proximally on the surface 316 of the flex circuit ribbon 102 than the second portion of the surface 316 of the flex circuit ribbon 102. A sufficiently small amount of stiffener 318 can be situated on a surface 316 of the flex circuit ribbon 102 at or near a distal end portion of the elongated member 100 so as to help provide a mechanical characteristic of an atraumatic distal tip portion of the elongated member 100.

FIGS. 5A-B show examples of elongated members 100A-B. The elongated member 100 can optionally include an interchangeable distal portion 520 (e.g., an electrically conductive end-user attachable or detachable elongated distal portion).

The interchangeable distal portion 520 can be attached to or detached from an immediately less distal portion of the elongated member 100, such as by an end-user. The interchangeable distal portion 520 can be configured to allow an end-user to electrically or mechanically couple or decouple the interchangeable distal portion 520 to or from an immediately more proximal portion of the flex circuit ribbon 102, such as shown in FIGS. 5A-B. The interchangeable distal portion 520 can be configured to provide access to the lumen 110 of the elongated member 100, such as a through lumen port 522.

FIG. 5C illustrates an example of a mating connector portion 521 of the elongated member 100. The mating connector portion 521 can include a recess 524, one or more pluralities of male or female electrical connection features 526A-B, and a flex circuit ribbon 102K, the flex circuit ribbon can include a plurality of mating female or male electrical connection features 528A. The mating connector portion 521 can include the connection features 526A-B that can be situated about the recess 524, such as shown in FIGS. 5B-C. The mating connection features 528A-B can be situated about the mating connector portion 521 of the elongated member 100. The connection features 526 can be configured to allow soldering or other technique of making physical contact between mating connection features 528. Secure engagement of a mating connection feature 528 can be achieved by configuring the connection features 526 with a flare, such as shown in FIG. 9B. Flaring can include widening the connection feature 526 as the connection feature 526 extends further away from a central axis of the lumen 110, the lumen port 522, or the elongated member 100. The connection feature 526 can be a zero insertion force connection feature (e.g., a connection feature that requires little or no applied external force to create a mechanical or electrical connection therewith). The connection feature 526 can include or be plated with gold or other suitable material, such as to reduce oxidation or increase the electrical conductivity or reliability of the electrical connection feature 526.

The flex circuit ribbon 102 can include multiple flex circuit ribbon portions, which can be electrically or mechanically bonded, affixed, or otherwise joined, such as by using a Z-axis adhesive (e.g., an anisotropic adhesive) or micro-soldering technique. This can permit the flex circuit ribbon 102 to be manufactured more cost efficiently than manufacturing each flex circuit ribbon 102 as a whole. Manufacturing a straight portion of the flex circuit ribbon 102 separate from a non-straight portion of the flex circuit ribbon 102 can allow for more flex circuit ribbon 102 to be manufactured in or on a panel than would be possible by manufacturing both straight and non-straight portion portions of the flex circuit ribbon 102 in or on the same panel. Separately manufacturing portions of the flex circuit ribbon 102 can allow a more expensive flex circuit ribbon 102, such as a high-density flex circuit ribbon 102 (e.g., including a multi-layer, ultra-fine conductor, a plated through hole, or a combination thereof) to be manufactured in or on smaller panels. An end portion of the flex circuit ribbon 102, such as a distal portion or a proximal portion, can be manufactured separate from an intermediate or other portion of the flex circuit ribbon 102 to be coupled to the end portion of the flex circuit ribbon 102.

More examples of interchangeable distal or other portions are presented herein, such as in the "Interchangeable Distal Portion" section of this document.

FIGS. 6A-B show examples of a connector 630, such as can be included in or connected to the elongated member 100 at one or both ends. The connector 630 can be configured to electrically couple to the flex circuit ribbon 102, or to provide access to the lumen 110, such as using lumen port 522, or both. The connector 630 can include a plurality of male or female electrical connection features 526A. The connection features 526A can be configured to be respectively individually coupled to individual conductors 108 of the flex circuit ribbon 102, such as by connecting one or more connection features 526A to one or more mating connection features 528. The lumen port 522 can be configured to include a perimeter of substantially the same dimension(s) as that of the lumen 110. The flex circuit ribbon 102 can include an end portion 631 that can be configured to electrically or mechanically couple to the connector 630, such as shown in FIG. 6C.

More examples of connectors are presented herein, such as in the "Connector" section of this document.

FIGS. 7A-B show examples of interface connectors 736. The interface connector 736 can be configured to be electrically and mechanically coupled to the connector 630. The interface connector 736 can be configured to provide access to the lumen 110, such as through lumen port 522. The interface connector 736 can include a plurality of male or female electrical connection features 526D-E. The connection features 526D-E can be configured to be respectively individually coupled to one or more mating connection features 526C of the connector 630.

More examples of interface connectors are presented herein, such as in the "Interface Connector" section of this document.

FIG. 8 shows an example of a technique 800 of making an at least partially implantable biocompatible catheter or other elongated member 100. At 802, a flex circuit ribbon 102, including at least one conductor 108, can be situated between an elongated inner portion 104 and an elongated outer portion 106 of the elongated member 100. This can include situating the flex circuit ribbon 102 between an outer surface 105 of the elongated inner portion 104 and an inner surface of the elongated outer portion 106. For example, this can include winding the flex circuit ribbon 102 helically about the outer surface 105 of elongated inner portion 104, then forming the elongated outer portion 106 thereupon. Or, this can include winding the flex circuit ribbon 102 helically, then molding or otherwise forming the elongated inner portion 104 and the elongated outer portion 106 together, about the wound flex circuit ribbon 102.

At 804, the inner portion 104 and the outer portion 106 can optionally be affixed together between portions of the flex circuit ribbon 102. The affixing can include gluing, bonding, adhering, heat shrinking, compressing, or other technique of affixing the elongated inner portion 104 to the elongated outer portion 106. The affixing can include helically bonding the inner portion 104 to the outer portion 106 between helically wound portions of the flex circuit ribbon 102.

At 806, the inner portion 104 and the outer portion 106 can optionally be integrally formed, such as using injection molding, three dimensional (3D) printing, or other technique. Situating the flex circuit ribbon 102 can occur concurrently with integrally forming the inner portion 104 and the outer portion 106 with the flex circuit ribbon 102 situated therebetween.

A mandrel 140 can be situated in a lumen 110 of the inner portion 104 before affixing or integrally forming the inner portion 104 to the outer portion 106, such as to allow the lumen 110 to remain substantially unchanged. The inner portion 104 can be formed around the mandrel 140 to form the lumen 110.

Heat shrink tubing can be placed around the outer surface 105 of the elongated outer portion 106. Heat can be applied to the heat shrink tubing to compress, bond, fuse, or otherwise join the elongated outer portion 106 and elongated inner portion 104 together between portions of the flex circuit ribbon 102. The heat shrink tubing can be selectively removed, such as to expose one or more electrical contacts 112 or a portion of an outer surface 568 (see FIG. 5) of the elongated outer portion 106. Such removal can include grinding, such as centered grinding (e.g., grinding with placing the object to be ground on a spindle) center-less grinding (e.g., grinding without placing the object to be ground on a spindle), or other process.

At 808, one or more electrical contacts 112 can be connected to respective one or more conductors 108 of the flex circuit ribbon 102.

The flex circuit ribbon 102 can increase the lifespan of the elongated member 100 as compared to an elongated member 100 without the flex circuit ribbon 102. The flex circuit ribbon 102 can help the elongated member 100 resist fatigue, such as by helping the elongated member 100 become more durable (e.g., resistant to failure from tensile and compression loads).

Selectively situating the stiffener 318 to create an atraumatic distal tip at a distal end of the elongated member 100 can avoid a need to include a more complex and more expensive atraumatic distal tip, which could also otherwise be more likely to break off of the elongated member 100.

Helically winding the flex circuit ribbon 102 about the inner portion 104 of the elongated member 100 that includes the lumen 110, can help provide mechanical support for the lumen 110, such as to help the lumen 110 withstand pressure exerted on the lumen 110 by material therein, or to help avoid potential kinking of the elongated member 110 that may otherwise occur, e.g., due in part to the lumen 110.

Connector

FIGS. 6A-B show examples of the connector 630 that can include a first end portion 642 and a second end portion 644.

The first end portion 642 can include male or female electrical connection features 526C or 526J that can be configured to electrically or mechanically couple to or securely engage one or more mating female or male electrical connection features 528B of the flex circuit ribbon 102, such as shown in FIG. 6C. The first end portion 642 can provide access to the lumen 110, such as through the lumen port 522A.

One or more male or female electrical connection features 526J at or near the first end portion 642 can respectively be individually electrically coupled to a corresponding one or more female or male electrical connection features 526C at or near a second end portion 644 of the connector 630. The connection features 526 can be evenly or otherwise circularly distributed about a lumen port 522, such as shown in FIG. 6B.

The connection features 526 can be configured to electrically couple to one or more electrical contacts or pads 196 on or in the flex circuit ribbon 102, such as shown in FIG. 1A. The electrical pad 196 can be exposed by selectively removing one or more portions of heat shrink tubing covering the electrical pad 196; selectively removing one or more portions of the outer portion 106 of the elongated member 100 covering the electrical pad 196; a combination thereof.

The lumen port 522 can be "in line" (e.g., overlapping or concentric) with the lumen 110, such as to allow a wire or mechanical or electrical device to be inserted through the lumen port 522 and into the lumen 110. Such a configuration may allow insertion without turning or twisting the wire or device.

Figure 9A:
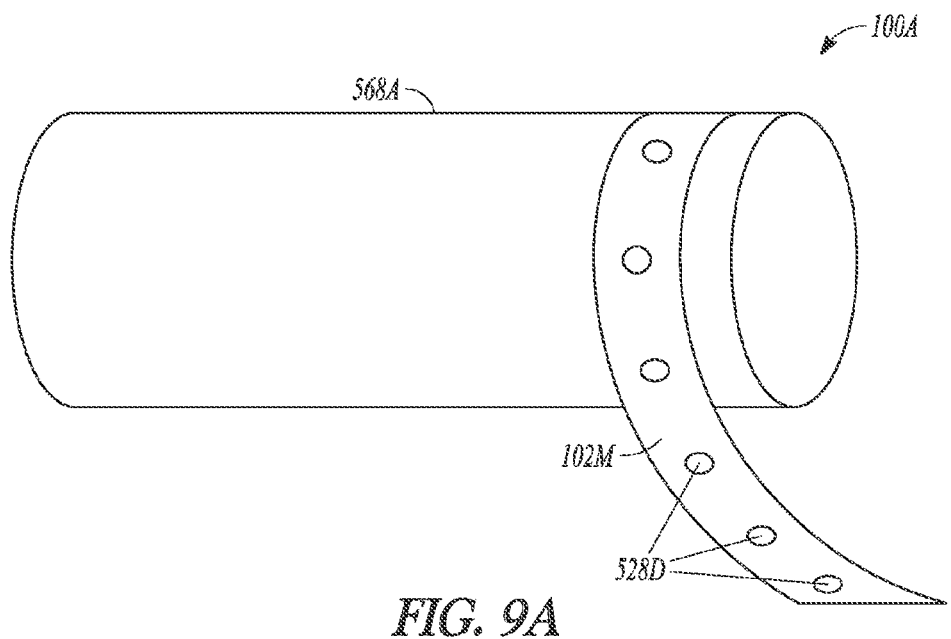
FIG. 9A illustrates a side view of an example of an elongated member.
Figure 9B:
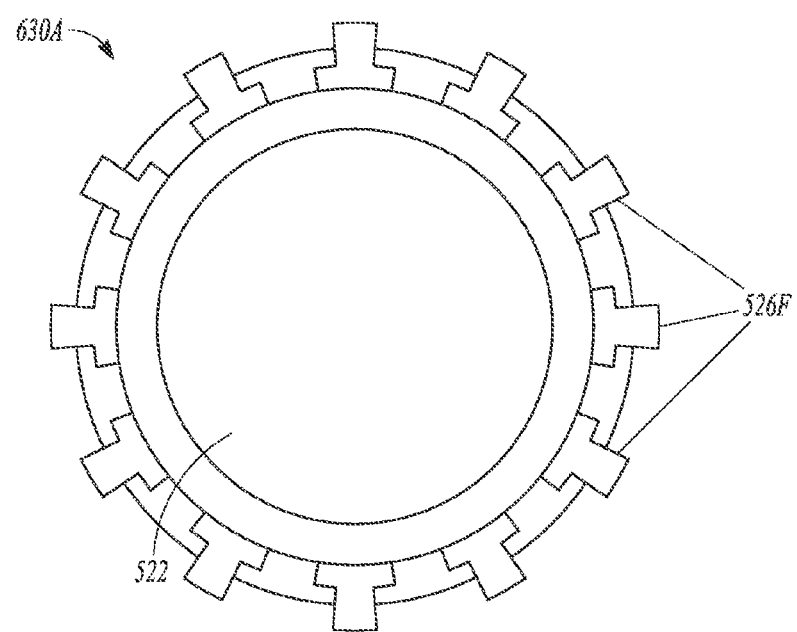
FIG. 9B illustrates an end view of an example of a connector.
Figure 9C:
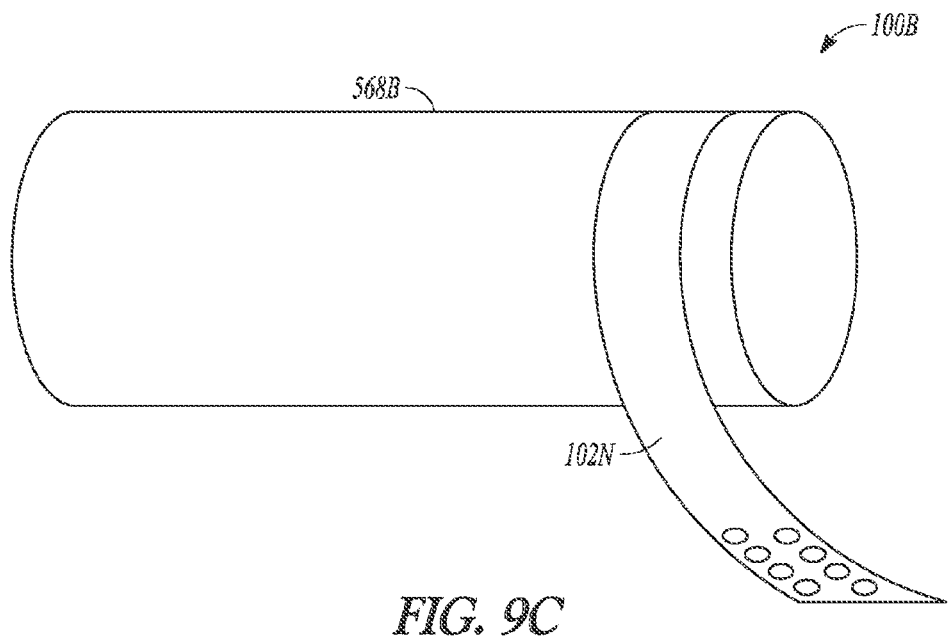
FIG. 9C illustrates a side view of an example of an elongated member.

FIGS. 9A and 9C show examples of elongated members 100A-B. A flex circuit ribbon 102M-N can wind out of an outer surface 568A-B of the elongated member 100A-B or can include mating connection features 528C-D, such as shown in FIGS. 9A and 9C.

Figure 9D:
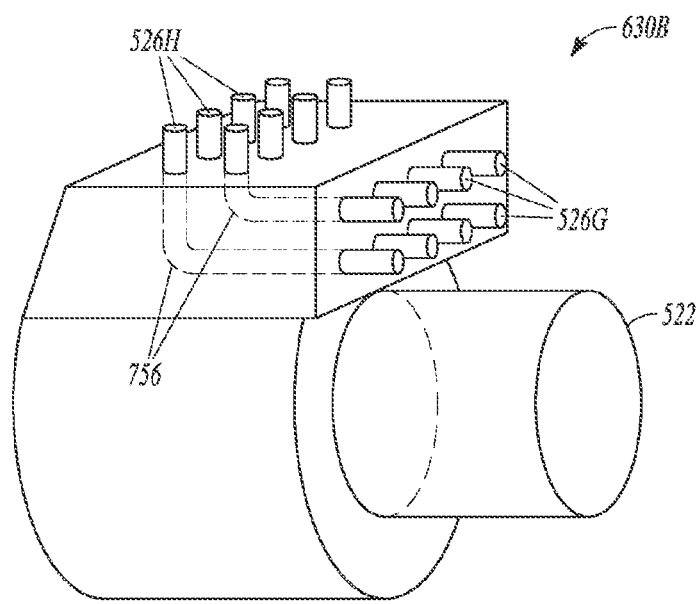
FIG. 9D illustrates an end view of an example of a connector.

FIGS. 9B and 9D show examples of connectors 630A-B that can include connection features 526A-C or a lumen port 934A-B. The connector 630 can be configured to electrically or mechanically couple to a proximal or distal end portion of the elongated member 100.

The connector 630 can be configured as a quick-connect connector, such as configured to be selectively attached to and detached from the elongated member 100. The quick-connect connector can be configured substantially similar to the connector 630A.

The connection features 526A-C can extend outward (e.g., radially outward) from, or can be evenly or otherwise circularly evenly about, the lumen port 522. The connection features 526 can be evenly or otherwise linearly distributed, such as shown in FIG. 9D. The connection features 526 can be configured to permanently securely engage mating connection features 528 of the flex circuit ribbon 102. Permanently securely engaging can include soldering, adhering, bonding, gluing, affixing, or otherwise permanently joining. The connection features 526B can be linearly evenly distributed longitudinally perpendicular to corresponding connection features 526C, such as shown in FIG. 9D. The mating connection feature 528 can include at least partially surrounding gold, nickel, gold-nickel, or other conductive material.

Figure 10:
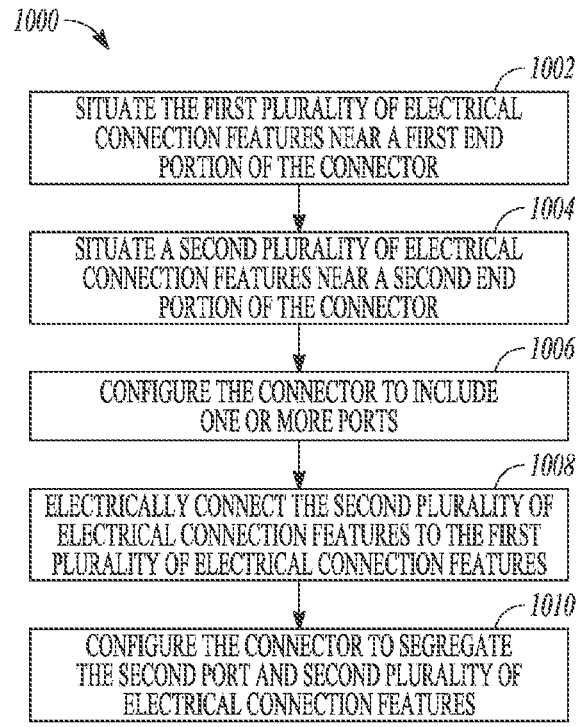
FIG. 10 illustrates an example of a technique of making a connector.

FIG. 10 shows an example of a technique 1000 of making the connector 630. Male or female electrical connection features 526 can be electrically or mechanically coupled to desired conductors 108. This can include electrically or mechanically coupling the first male or female electrical connection features 526J to a mating female or male electrical connection feature 528 of a flex circuit ribbon 102.

At 1002, the first connection features 526J can be situated at or near a first end portion 642 of the connector 630.

At 1004, a second plurality of electrical connection features 526C can be situated near a second end portion 644 of the connector 630.

At 1006, access to a first lumen 110 can be provided, such as by configuring the connector 630 with one or more lumen ports 522. The second plurality male or female electrical connection features 526C can be situated at or near a second end portion 644 of the connector 630.

At 1008, the first electrical connection features 526J can be respectively individually electrically coupled to corresponding second electrical connection features 526C. The connection can be made by electrically connecting an electrically conductive member 750 to one of the first connection features 526J and to one of the second connection features 526C, such as shown in FIG. 9D.

At 1010, the connector 630 can be configured to segregate access to the lumen 110 and the first or second connection features 526. Segregating can include allowing a direct access or connection to the lumen 110 without affecting access to the connection features 526, such as by configuring the connector 630 to include enough distance between the lumen port 522 and the connection features 526 nearest to the lumen port 522.

The connector 630 can be configured as a quick-connect connector, such as to allow the elongated member 100 to be used as a guide-wire. A user can detach such a connector 630 from the elongated member 100, can slide an object over the elongated member 100, and can re-attach the connector 630 to the elongated member 100.

Interface Connector

FIGS. 7A-B show examples of interface connectors 736 that can include a first end portion 752, a second end portion 753, a lumen port 522, one or more first male or female electrical connection features 526D, or one or more second male or female electrical connection features 526E.

The first end portion 752 can be configured to electrically or mechanically couple to a mating first connector, such as connector 630. The first end portion 752 can be configured to electrically and mechanically couple to the proximal end of the elongated member 100. The first connection features 526D can be situated at least partially within or near the first end portion 752.

The second end portion 753 can be configured to electrically or mechanically couple to a mating second connector. The second connection features 526D can be situated at least partially within or near the second end portion 753. The connection features 526 can be configured to electrically or mechanically couple to a multi-row mating female or male electrical connection feature, such as shown in FIG. 7B.

The lumen port 522 can be configured to provide access to a first lumen 110 or lumen port 522, at or near the first end portion 752, and a second lumen 110 or lumen port 522, at or near the second end portion 753. The lumen port 522 can be configured to securely engage the lumen 110. The lumen port 522 can include one or more protrusions 754 extending outwardly therefrom, such as shown in FIG. 7A. The one or more protrusions 754 can allow for secure engagement of the lumen 110. Securely engaging a lumen 110 can help make it more difficult to remove the lumen 110 from the lumen port 522, such as by accidentally bumping the lumen 110 or an object mechanically coupled thereto.

The connection features 526D-E can be configured substantially similar to the connection features 526C. The connection features 526D can be respectively individually electrically coupled to a corresponding one of connection features 526E. Such a connection can be established by connecting an electrically conductive member 750 within the interface connector 736 to one or more of the first connection features 526D and to one or more of the second connection features 526E, such as shown in FIG. 7A.

The connection features 526 can be evenly or otherwise linearly distributed or they can be configured to electrically connect to a multi-row connector, such as shown in FIG. 7B.

The interface connector 736 can include a protrusion 756 around at least a portion of a perimeter of the first end portion 752 or the second end portion 753. The protrusion 756 can be configured to surround a portion of a mating connector coupled to the interface connector 736. The protrusion 756 can increase the strength of a connection between the interface connector 736 and the mating connector. The protrusion 756 can protect the connection between the interface connector 736 and another connector, such as by protecting from external elements or forces.

Figure 11:
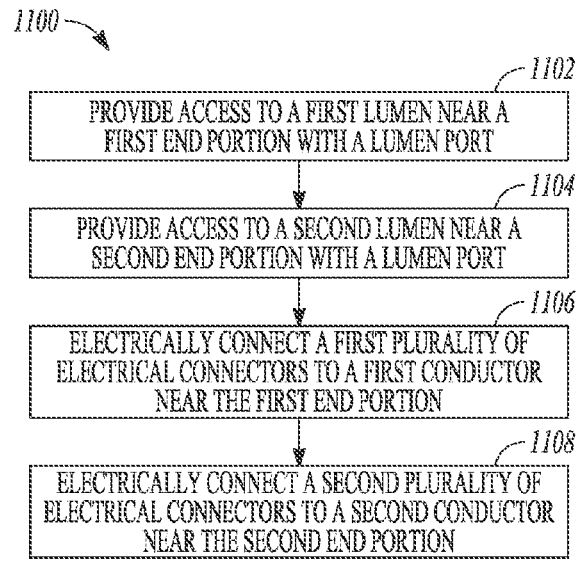
FIG. 11 illustrates an example of a technique of using an interface connector.

FIG. 11 shows an example of a technique 1100 of using the interface connector 736. At 1102, access to a first lumen 110 near a first end portion 752 of an interface connector 736 can be provided, such as by using the lumen port 522. At 1104, access to a second lumen 110 near a second end portion of the interface connector 736 can be provided, such as by using the lumen port 522.

At 1106, the connection features 526 can be electrically connected to one or more conductors 108 near the first end portion 752, such as electrically connecting to conductors 108 of the flex circuit ribbon 102. At 1108, the connection features 526 can be electrically connected to a conductor at or near the second end portion 753 of the interface connector 736. The first end portion 752 of the interface connector 736 can be coupled to the proximal end of a catheter or other elongated member 100.

Interchangeable Distal Portion

Figure 12A:
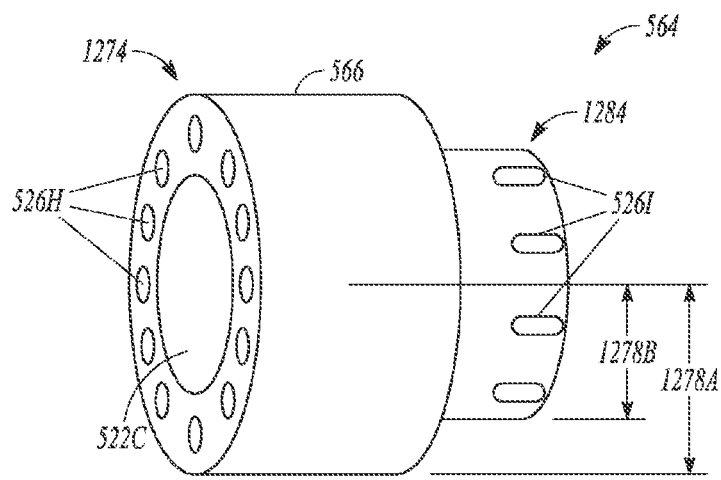
FIG. 12A illustrates a side view of an example of a connector portion of an interchangeable distal portion.
Figure 12B:
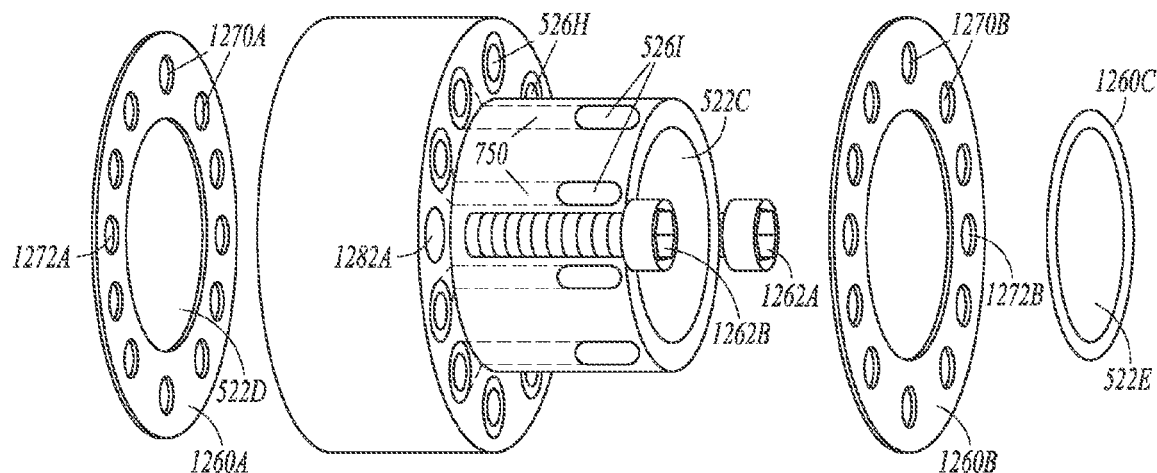
FIG. 12B illustrates an exploded view diagram of an example of a connector portion of an interchangeable distal portion.
Figure 12C:
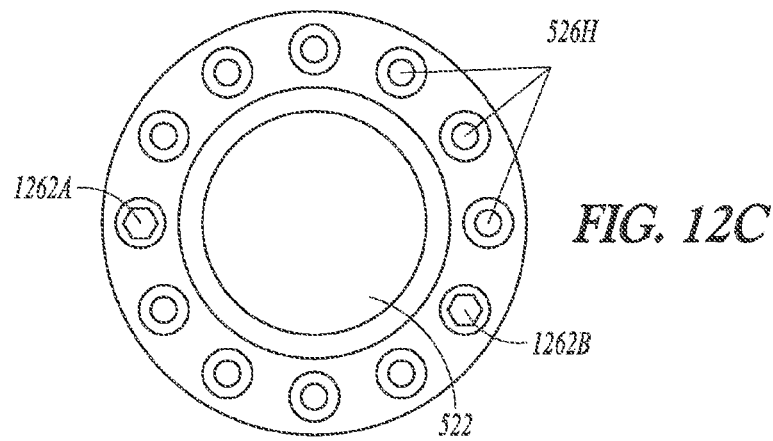
FIG. 12C illustrates an end view of an example of a connector portion of an interchangeable distal portion.
Figure 12D:
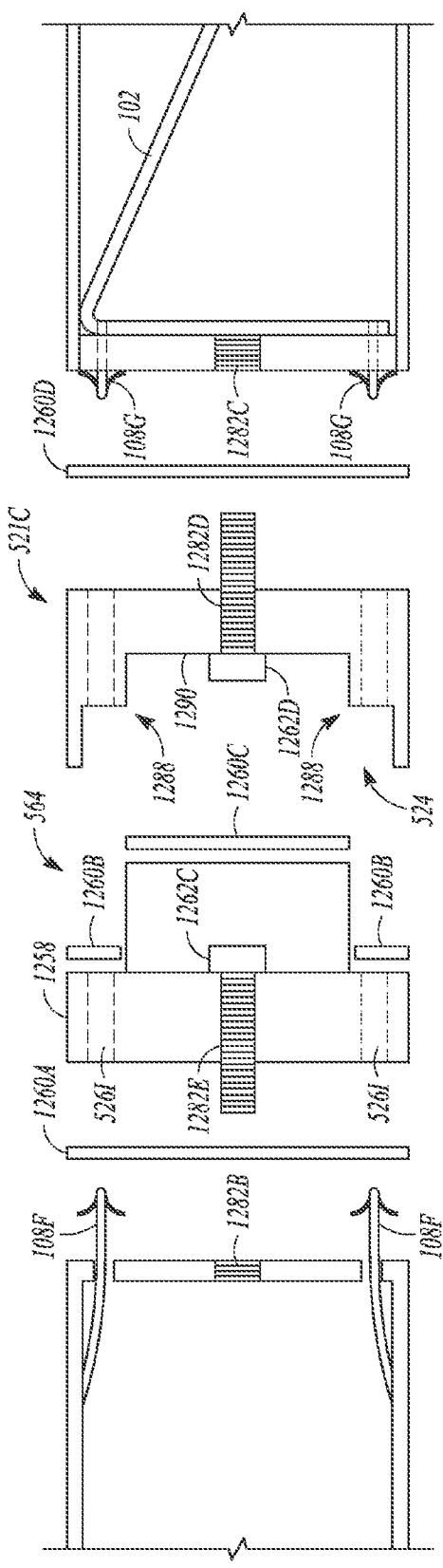
FIG. 12D illustrates a side view of an example of an elongated member.

FIG. 5A shows an example of an interchangeable distal portion 520. FIGS. 12A-D show examples of one or more connector portions 564 of the interchangeable distal portion 520. The interchangeable distal portion 520 can be configured to be biocompatible or at least partially implantable. While FIGS. 5A and 12D depict the interchangeable distal portion 520 as including a male electrical connection feature and a corresponding elongated member 100 as including a mating female electrical connection feature, the interchangeable distal portion 520 can include a female electrical connection feature and the corresponding elongated member 100 can include a mating male electrical connection feature.

A catheter can include the elongated member 100 and the interchangeable distal portion 520. The connector portion 564 can be configured to be electrically or mechanically coupled to (e.g., engage) the elongated member 100, such as at a portion of the catheter that is less distal than the interchangeable distal portion 520. The connector portion 564 can be configured to electrically couple to a conductor 108F and to provide access to the lumen 110, such as through a lumen port 522A. The connector portion 564 can be configured to allow an end-user to selectively attach or selectively detach the interchangeable distal portion 520 to or from the elongated member 100. The connector portion 564 can be configured such that a portion of the outer most surface 566 of the connector portion 564 is substantially flush, such as laterally, with a portion of the outer surface 568 of the elongated member 100 when the interchangeable distal portion 520 is attached to the elongated member 100.

The connector portion 564 can be configured to provide a sealed coupling at a proximal end of the interchangeable distal portion 520. The connector portion 564 can be configured to make contact with a first gasket 1260A situated appropriately, such as shown in FIG. 12B, such as to create an airtight seal between the connector portion 564 and another portion of the interchangeable distal portion 520, such as shown in FIG. 5A. The first gasket 1260A can be configured with one or more holes 1270A, such as to allow a conductor 108 to pass therethrough. The first gasket 1260A can be configured to provide access to the lumen 110, such as through a lumen port 522D. The first gasket 1260A can include a screw hole 1272A configured to allow a screw 1262A-B to pass therethrough or engage threads of the screw 1262A-B.

The connector portion 564 can include a first connector portion 1274. The first connector portion 1274 can include a plurality of male or female electrical connection features 526H that can be configured to electrically or mechanically engage the one or more conductors 108. The first connector portion 1274 can be configured to provide access to the lumen 110, such as through a lumen port 522C. The first connector portion 1274 can include a first center to edge width 1278A. The first connector portion 1274 can be configured to be substantially circular and the first center to edge width 1278A can be a radius, such as shown in FIG. 12A. The connector portion 564 can include a stepped profile, such as to align and mate with a corresponding profile of an elongated less distal portion of the catheter, such as shown in FIG. 12D.

The first connector portion 1274 can include at least one screw hole 1282A. The screw hole 1282A can overlap or be concentric with another screw hole 1282B-E so as to allow a screw 1262 to be screwed into two or more screw holes 1282A-E, concurrently. Such a configuration can allow a screw 1262 to secure the connector portion 564 to another portion of the interchangeable distal portion 520.

The connector portion 564 can include a second connector portion 1284 that includes a plurality of male or female electrical connection features 526A. Connection features 526A can be configured to electrically or mechanically couple to connection features 526B of the elongated member 100. The connection features 526H can be electrically coupled to the connection features 526A, such as through an electrically conductive member 750, such as shown in FIG. 12B. The second connector portion 1284 can be configured to provide access to the lumen 110, such as through a lumen port 522C. The second connector portion 1284 can include a second center to edge width 1278B that can be smaller than the first center to edge width 1278A. The second connector portion 1284 can be configured to be substantially circular and the second center to edge width 1278B can be a radius, such as shown in FIG. 12A.

The connector portion 564 can be configured to make sufficient contact with a second gasket 1260B, such as shown in FIG. 12B. The second gasket 1260B can be configured to seal a coupling between the first connector portion 1274 and a portion 1288 of the elongated member 100, such as at a proximal interface of the interchangeable distal portion 520. The second gasket 1260B can be configured to surround a portion of the second connector portion 1284. The first gasket 1260A can be configured to be substantially similar to second gasket 1260B, and vice versa.

The connector portion 564 can be configured to make sufficient contact with a third gasket 1260C, such as shown in FIG. 12B. The third gasket 1260C can be configured to seal a coupling between the first connector portion 1274 and a portion 1290 of the elongated member 100, such as at a proximal end of the interchangeable distal portion 520. The third gasket 1260C can be configured to provide access to the lumen 110, such as through a lumen port 522E. The connector portion 520 can include the first gasket 1260A, second gasket 1260B, and third gasket 1260C.

The connector portion 564 can be positioned so that it does not contact a specific area or object, such as tissue, when the corresponding interchangeable distal portion 520 is in use. For example, the interchangeable distal portion 520 can be manufactured sufficiently long so that the connector portion 564 does not contact a heart or the connector portion 564 remains outside of a body, when the interchangeable distal portion 520 is in use.

A conductor 108 can be fed to the connector portion 564 and can be soldered, or otherwise electrically or mechanically coupled, to connection feature 526.

The elongated member 100 can be configured to include a mating connector portion 521A-C that can be configured to be electrically or mechanically coupled to the interchangeable distal portion 520, such as by connecting the mating connector portion 521A-C to the connector portion 564. The mating connector portion 521A-C of the elongated member 100 can include a screw hole 1282D configured to engage a screw 1262D. The recession 524 can be configured to receive at least a portion of the connector portion 564. The mating connector portion 521C of the elongated member 100 can be configured to securely engage a fourth gasket 1260D when the fourth gasket 1260D is situated appropriately, such as shown in FIG. 12D. The mating connector portion 521 can be configured to accommodate interconnect requirements for a range of interchangeable distal portions 520 such as a variety of shapes, sizes, and number of electrical connection features 526, and sizes and shapes of lumen ports 522.

The screw holes 1282C-D can be configured to allow a single screw 1262 to be screwed into at least two of the screw holes 1282C-D so as to secure the mating connector portion 521 to another portion of the elongated member 100.

One or more conductor(s) 108B of the elongated member 100 can be fed to the connector portion 521 of the elongated member 100 and soldered or otherwise electrically or mechanically coupled to the connector portion 521.

FIGS. 12A-D show examples of connector portions 564 configured to connect to the elongated member 100. The connector portion 564 can be configured in different ways to allow the interchangeable distal portion 520 to be mechanically or electrically connected to or disconnected from the elongated member 100. For example, the screw holes 1282 of the connector portion 564 or mating connector portion 521 could be posts, such as snap-in or molded posts, configured to be inserted into a mating hole in the mating connector portion 521 or connector portion 564. FIGS. 12A-D show connection points between the interchangeable distal portion 520 and the elongated member 100 situated laterally along a circumference, however electrical connection features 526 may be situated longitudinally differently along electrically conductive member 750 or within the first connector portion 1274 or the second connector portion 1284. FIGS. 12A-D show gaskets 1260 that provide a way to seal (e.g., keep fluids from inside or outside the elongated member 100 from leaking into an area where there can be current flowing or an electrical coupling or connection) connections between the connector portion 564 and the mating connector portion 521. Such sealing could be achieved using liquid sealant, o-rings, an interchangeable distal portion 520 and elongated member 100 made of sufficiently malleable plastics, a bonding adhesive, or configuring the surfaces at an interface between the interchangeable distal portion 520 and the elongated member 100 such that when they are in contact a seal can be created, among others.

Figure 12E:
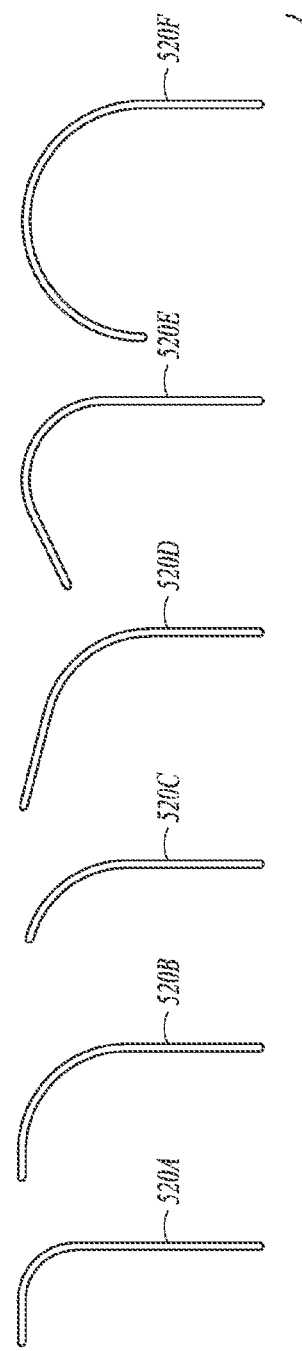
FIG. 12E illustrates examples of interchangeable distal portions.

FIG. 12E shows various interchangeable distal portions 520 including various shapes. The interchangeable distal portion 520 can include a Josephson shape, a Cournand shape, a conduction study shape, a D'Amato shape, or a K-Curve shape, such as shown with interchangeable distal portions 520A-F, respectively.

The elongated member 100 with the interchangeable distal portion 520, such as a non-steerable catheter, can help a physician perform an operation. Sometimes an operation can call for different distal curves to access different areas or objects, such as areas or objects of the human body. In such an operation, a physician can use different elongated members 100 with different distal curves. The elongated member 100 configured to attach to or detach from the interchangeable distal portion 520 can allow a physician to use the same base elongated member 100 with multiple interchangeable distal portions 520 to perform the same operation that calls for elongated members 100 with different distal curves. In this manner the cost of the tools to perform the operation can be reduced as the operation can be performed with just a single elongated member 100 and multiple interchangeable distal portions 520, rather than multiple separate elongated members 100 with different distal curves.

The interchangeable distal portion 520 can include substantially the same elements as the elongated member 100. For example, the interchangeable distal portion can include an elongated inner portion 104, an elongated outer portion 106, a flex circuit ribbon 102, one or more electrical contacts 112, or a lumen 110.

An interchangeable distal portion 520 can be configured for applications such as electro-stimulation, ablation, drug delivery, or other applications, by configuring the electrical contacts 112, lumen 110, one or more conductors 108, or stiffener 318, accordingly.

Figure 13:
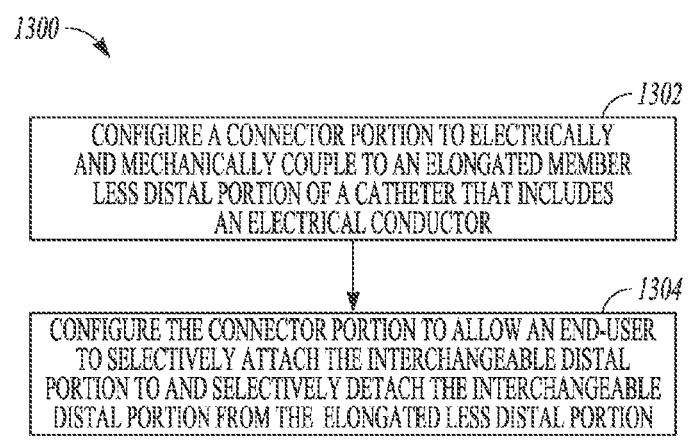
FIG. 13 illustrates an example of a technique of making an interchangeable distal portion.

FIG. 13 is an example of a technique 1300 of making an interchangeable distal portion 520 of the elongated member 100. At 1302, a connector portion 564 of the interchangeable distal portion 520 can be configured to electrically and mechanically couple to an elongated less distal portion of a catheter that includes an electrical conductor.

At 1304, connector portion 564 can be configured to allow an end-user to selectively attach the interchangeable distal portion 520 to or selectively detach the interchangeable distal portion 520 from the elongated less distal portion of the catheter. The interchangeable distal portion 520 can be configured such that when the interchangeable distal portion 520 is attached to the elongated less distal portion of the catheter the interchangeable distal portion 520 is the most distal portion of the catheter. In one or more embodiments, the interchangeable distal portion 520 and elongated member 100 can be isodiametric.

ADDITIONAL NOTES AND EXAMPLES

Example 1 can include or use subject matter (such as an apparatus, a method, a means for performing acts, or a device readable memory including instructions that, when performed by the device, can cause the device to perform acts), such as can include or use an elongated inner portion, an elongated outer portion, and a flex circuit ribbon, including at least one conductor, the flex circuit ribbon situated between the inner portion and the outer portion, wherein the inner portion and the outer portion can be (1) affixed together between portions of the flex circuit ribbon or (2) integrally formed such that masses of the inner and outer portions can be joined together between portions of the flex circuit ribbon. The apparatus of Example 1 can include an electrical contact, configured to be exposed during use, the electrical contact included in or connected to the at least one conductor of the flex circuit ribbon.

Example 2 can include or use, or can optionally be combined with the subject matter of Example 1, to optionally include or use an at least partially implantable biocompatible catheter including the inner portion, the outer portion, the flex circuit ribbon, or the electrical contact, wherein at least one of: (1) the electrical contact can include an electrode, (2) the inner portion can include an elongated inner member including an outer surface (3) the outer portion can include an elongated tubular outer member including an inner surface, (4) the flex circuit ribbon can be situated between (i) the outer surface of the inner member and (ii) the inner surface of the outer member, and the flex circuit ribbon can be helically wound about the inner member, and (5) the inner member and the outer member can be bonded helically together between helically wound portions of the flex circuit ribbon.

Example 3 can include or use, or can optionally be combined with the subject matter of at least one of Examples 1-2, to optionally include or use a stiffener selectively situated on a surface of the flex circuit ribbon.

Example 4 can include or use, or can optionally be combined with the subject matter of at least one of Examples 1-3, to optionally include or use the stiffener selectively situated on the surface of the flex circuit ribbon to provide a specified stiffener pattern on the surface of the flex circuit ribbon.

Example 5 can include or use, or can optionally be combined with the subject matter of at least one of Examples 1-4, to optionally include or use a greater quantity of the stiffener situated on a first portion of the surface of the flex circuit ribbon than on a second portion of the surface of the flex circuit ribbon, wherein the first portion of the surface of the flex circuit ribbon can be longitudinally situated differently on the apparatus than the second portion of the surface of the flex circuit ribbon.

Example 6, can include or use, or can optionally be combined with the subject matter of at least one of Examples 1-5, to optionally include or use an end-user attachable or detachable elongated portion, configured to permit an end-user to (1) electrically couple the end-user attachable or detachable elongated portion to or (2) electrically decouple the end-user attachable or detachable elongated portion from, a portion of the flex circuit ribbon that can be longitudinally situated differently on the apparatus than a portion of the end-user attachable or detachable elongated portion.

Example 7, can include or use, or can optionally be combined with the subject matter of at least one of Examples 1-6, to optionally include or use a connector that can be configured to connect the end-user attachable or detachable elongated portion. The flex circuit ribbon of Example 7 can include a male or female electrical connection feature in a portion of the flex circuit ribbon situated about the connector. The male or female electrical connection feature of Example 7 can be configured to engage a mating female or male electrical connection feature of another connector.

Example 8, can include or use, or can optionally be combined with the subject matter of at least one of Examples 1-7, to optionally include or use a lumen. In Example 8, the apparatus can include a connector configured to be electrically coupled to the flex circuit ribbon. In Example 8, the connector can include a lumen port configured to provide access to the lumen.

Example 9, can include or use, or can optionally be combined with the subject matter of at least one of Examples 1-8, to optionally include or use a plurality of male or female electrical connection features configured to be respectively individually coupled to conductors of the flex circuit ribbon.

Example 10, can include or use, or can be optionally be combined with the subject matter of at least one of Examples 1-9, to optionally include or use a plurality of discrete electrodes situated about the flex circuit ribbon so as to provide a specified electric field distribution for the apparatus.

Example 11 can include or use, or can be optionally be combined with the subject matter of at least one of Examples 1-10, to include subject matter (such as an apparatus, a method, a means for performing acts, or a device readable memory including instructions that, when performed by the device, can cause the device to perform acts), such as can include or use situating a flex circuit ribbon, including at least one conductor, between an elongated inner portion and an elongated outer portion. Example 11 can optionally include or use (1) affixing the inner portion and the outer portion together between portions of the flex circuit ribbon or (2) integrally forming the inner portion and outer portion with the flex circuit ribbon situated therebetween such that masses of the inner and outer portions can be joined together between portions of the flex circuit ribbon. Example 11 can optionally include or use providing an electrical contact, configured to be exposed during use, at or connected to the at least one conductor of the flex circuit ribbon.

Example 12 can include or use, or can optionally be combined with the subject matter of at least one of Examples 1-11 to optionally include or use making an at least partially implantable biocompatible catheter. Example 12 can include or use wherein providing the electrical contact can include providing an electrode. Example 12 can optionally include or use wherein situating the flex circuit ribbon of can include situating the flex circuit ribbon between (1) an outer surface of an elongated inner member of the elongated inner portion and (2) an inner surface of an elongated tubular outer member of the elongated outer portion. Example 12 can optionally include or use wherein situating the flex circuit ribbon can include winding the flex circuit ribbon helically about the elongated inner member. Example 12 can optionally include or use wherein affixing the elongated inner portion and the elongated outer portion can include helically bonding the elongated inner member and the elongated outer member together between helically wound portions of the flex circuit ribbon.

Example 13 can include or use, or can optionally be combined with the subject matter of at least one of Examples 1-12, to optionally include or use selectively situating a stiffener on a surface of the flex circuit ribbon.

Example 14 can include or use, or can optionally be combined with the subject matter of at least one of Examples 1-13, to optionally include or use selectively patterning the stiffener on the surface of the flex circuit ribbon.

Example 15 can include or use, or can optionally be combined with the subject matter of at least one of Examples 1-14, to optionally include or use wherein selectively situating the stiffener on the surface of the flex circuit ribbon can include selectively situating a greater quantity of the stiffener on a first portion of the surface of the flex circuit ribbon than on a second portion of the surface of the flex circuit ribbon, wherein the first portion of the surface of the flex circuit ribbon can be longitudinally situated differently than the second portion of the surface of the flex circuit ribbon.

Example 16 can include or use, or can optionally be combined with the subject matter of at least one of Examples 1-15, to optionally include or use wherein situating the flex circuit ribbon can include situating the flex circuit ribbon about and outside of a lumen of the elongated inner portion. Example 16 can optionally include or use at least one of electrically coupling a connector to the flex circuit ribbon and providing access to the lumen of the elongated inner portion using a lumen port of the connector.

Example 17 can include or use, or can optionally be combined with the subject matter of at least one of Examples 1-16, to optionally include or use wherein coupling the connector can include electrically coupling a male or female electrical connection feature of the connector to the at least one conductor of the flex circuit ribbon.

Example 18 can include or use, or can optionally be combined with the subject matter of at least one of Examples 1-17, to optionally include or use electrically coupling an end-user attachable or detachable elongated portion to or electrically de-coupling the end-user attachable or detachable elongated portion from another portion of the apparatus.

Example 19 can include or use, or can optionally be combined with the subject matter of at least one of Examples 1-18, to optionally include or use wherein providing the electrical contact can include providing a plurality of discrete electrodes situated about the flex circuit ribbon so as to provide a specified electric field distribution for the apparatus.

Example 20 can include or use, or can be optionally be combined with the subject matter of at least one of Examples 1-19, to include subject matter (such as an apparatus, a method, a means for performing acts, or a device readable memory including instructions that, when performed by the device, can cause the device to perform acts), such as can include or use an at least partially implantable biocompatible catheter including an elongated inner portion, including an elongated tubular inner member including an outer surface and a lumen. Example 20 can optionally include or use an elongated outer portion, including an elongated tubular outer member including an inner surface. Example 20 can optionally include or use a flex circuit ribbon, including at least one conductor, the flex circuit ribbon disposed between (1) the outer surface of the elongated tubular inner member and (2) the inner surface of the elongated tubular outer member, the flex circuit ribbon helically wound about the elongated inner member, wherein the inner portion and the outer portion can be (1) affixed together between portions of the flex circuit ribbon so as to helically bond the inner member and the outer member together between helically wound portions of the flex circuit ribbon or (2) integrally formed such that the flex circuit ribbon can be situated therebetween such that masses of the inner and outer portions may be joined together between portions of the flex circuit ribbon. Example 20 can optionally include or use an electrical contact, configured to be exposed during use, the electrical contact can be in or connected to the at least one conductor of the flex circuit ribbon, the electrical contact including a plurality of discrete electrodes situated about the flex circuit ribbon so as to provide a specified electric field distribution for the apparatus. Example 20 can optionally include or use a stiffener, selectively situated on the surface of the flex circuit ribbon to provide a specified stiffener pattern on the surface of the flex circuit ribbon, wherein a greater quantity of the stiffener can be situated on a first portion of the surface of the flex circuit ribbon than on a second portion of the surface of the flex circuit ribbon, wherein the first portion of the surface of the flex circuit ribbon can be longitudinally situated differently on the apparatus than the second portion of the surface of the flex circuit ribbon. Example 20 can optionally include or use a connector configured to be electrically coupled to the flex circuit ribbon, the connector can include a lumen port configured to provide access to the lumen, and the connector can include a plurality of male or female electrical connection features, configured to be respectively individually coupled to conductors of the flex circuit ribbon. Example 20 can optionally include or use an end-user attachable or end-user detachable elongated portion, configured to permit an end-user to (1) electrically couple the end-user attachable or detachable elongated portion to or (2) electrically decouple the end-user attachable or detachable elongated portion from, a portion of the flex circuit ribbon longitudinally situated differently on the apparatus than a portion of the end-user attachable or detachable elongated portion. Example 20 can optionally include or use a second connector, configured to connect the end-user attachable or end-user detachable elongated portion. Example 20 optionally can include or use the flex circuit ribbon including a male or female electrical connection feature of a portion of the flex circuit ribbon that can be situated about the second connector, and wherein the male or female electrical connection feature can be configured to engage a mating female or male electrical connection feature on another connector.

Example 21 can include or use, or can be optionally be combined with the subject matter of at least one of Examples 1-20, to include subject matter (such as an apparatus, a method, a means for performing acts, or a device readable memory including instructions that, when performed by the device, can cause the device to perform acts), such as can include or use a first end portion, including a first plurality of male or female electrical connection features, the first plurality of male or female electrical connection features configured to connect to a first plurality of mating female or male electrical connection features, the first end portion including a first lumen port, the first lumen port configured to provide access to a first lumen. Example 21 can optionally include or use a second end portion, including a second plurality of male or female electrical connection features, the second plurality of male or female electrical connection features configured to connect to a second plurality of mating female or male electrical connection features, the second end portion including a second lumen port, the second lumen port configured to provide access to a second lumen.

Example 22 can include or use, or can optionally be combined with the subject matter of at least one of Examples 1-21, to optionally include or use the first plurality of male or female electrical connection features wherein the first plurality of male and female electrical connection features can be configured to electrically couple to a male or female electrical connection feature of a flex circuit ribbon of a catheter. Example 22 can optionally include or use the first plurality of male or female electrical connection features wherein the first plurality of male or female electrical connection features can be configured to respectively be electrically connected to a male or female electrical connection feature of the second plurality of male or female electrical connection features. Example 22 can optionally include or use the second plurality of male or female electrical connection features wherein the second plurality of male or female electrical connection features can be circularly distributed about the second lumen port.

Example 23 can include or use, or can optionally be combined with the subject matter of at least one of Examples 1-22, to optionally include or use the first plurality of male or female electrical connection features wherein the first plurality of male and female electrical connection features can be configured to electrically couple to a female or male electrical connection feature of a flex circuit ribbon.

Example 24 can include or use, or can optionally be combined with the subject matter of at least one of Examples 1-23, to optionally include or use the first plurality of male or female electrical connection features wherein the first plurality of male and female electrical connection features can be configured to respectively be electrically connected to an electrical connection feature of the second plurality of male or female electrical connection features.

Example 25 can include or use, or can optionally be combined with the subject matter of at least one of Examples 1-24, to optionally include or use the second plurality of male or female electrical connection features wherein the second plurality of male or female electrical connection features can be circularly distributed about the second lumen port.

Example 26 can include or use, or can optionally be combined with the subject matter of at least one of Examples 1-25, to optionally include or use the first or second lumen port including a protrusion extending outwardly from the first or second lumen port, the protrusion configured to engage the first or second lumen.

Example 27 can include or use, or can optionally be combined with the subject matter of at least one of Examples 1-26, to optionally include or use the first plurality of male or female electrical connection features wherein the first plurality of male or female electrical connection features (1) can be circularly distributed about the first lumen port and (2) extends radially outward from the first lumen port.

Example 28 can include or use, or can optionally be combined with the subject matter of at least one of Examples 1-27, to optionally include or use the connector wherein the connector can be configured as a quick-connect connector configured to be attached to and detached from an electrically conductive elongated tubular member by an end-user.

Example 29 can include or use, or can optionally be combined with the subject matter of at least one of Examples 1-28, to optionally include or use the first plurality of male or female electrical connection features wherein the first plurality of male or female electrical connection features can be configured to permanently respectively engage a female or male connection feature of the flex circuit ribbon.

Example 30 can include or use, or can optionally be combined with the subject matter of at least one of Examples 1-29, to optionally include or use the first plurality of male or female electrical connection features wherein the first plurality of male or female electrical connection features can be linearly distributed.

Example 31 can include or use, or can be optionally be combined with the subject matter of at least one of Examples 1-30, to include subject matter (such as an apparatus, a method, a means for performing acts, or a device readable memory including instructions that, when performed by the device, can cause the device to perform acts), such as can include or use situating a first plurality of male or female electrical connection features near a first end portion of the connector or situating a second plurality of male or female electrical connection features near a second end portion of the connector. Example 31 can optionally include or use configuring the connector to include (1) a first lumen port near the first end portion of the connector and (2) a second lumen port near the second end portion of the connector. Example 31 can optionally include or use configuring the second plurality of male or female electrical connection features to be respectively coupled to the first plurality of male or female electrical connection features or configuring the connector to segregate the second lumen port from the second plurality of male or female electrical connection features.

Example 32 can include or use, or can optionally be combined with the subject matter of at least one of Examples 1-31, to optionally include or use configuring the first plurality of male or female electrical connection features to respectively electrically couple to at least one conductor of a flex circuit ribbon of a catheter. Example 32 can optionally include or use circularly distributing the second plurality of electrical connection features about the second lumen port. Example 32 can optionally include or use wherein configuring the second plurality of male or female electrical connection features to be respectively coupled to the first plurality of male or female electrical connection features includes electrically configuring the second plurality of male or female electrical connection features to be respectively electrically coupled to the first plurality of male or female electrical connection features.

Example 33 can include or use, or can optionally be combined with the subject matter of at least one of Examples 1-32, to optionally include or use configuring the first plurality of male or female electrical connection features to respectively electrically couple to at least one conductor of a flex circuit ribbon.

Example 34 can include or use, or can optionally be combined with the subject matter of at least one of Examples 1-33, to optionally include or use wherein configuring the second plurality of male or female electrical connection features to be respectively coupled to the first plurality of male or female electrical connection features includes configuring the second plurality of male or female electrical connection features to be respectively electrically coupled to the first plurality of male or female electrical connection features.

Example 35 can include or use, or can optionally be combined with the subject matter of at least one of Examples 1-34, to optionally include or use circularly distributing the second plurality of electrical connection features about the second lumen port.

Example 36 can include or use, or can optionally be combined with the subject matter of at least one of Examples 1-35, to optionally include or use engaging a female or male electrical connection feature in a flex circuit ribbon using an electrical connection feature of the first plurality of electrical connection features.

Example 37 can include or use, or can optionally be combined with the subject matter of at least one of Examples 1-36, to optionally include or use circularly distributing the first plurality of electrical connection features about the first lumen port such that the first plurality of electrical connection features extends radially outward from the first lumen port.

Example 38 can include or use, or can optionally be combined with the subject matter of at least one of Examples 1-39, to optionally include or use configuring the connector as a quick-connect connector to be attached to and detached from an electrically conductive elongated tubular member by an end-user.

Example 39 can include or use, or can optionally be combined with the subject matter of at least one of Examples 1-38, to optionally include or use linearly distributing the first plurality of electrical connection features.

Example 40 can include or use, or can be optionally combined with the subject matter of at least one of Examples 1-39, to include subject matter (such as an apparatus, a method, a means for performing acts, or a device readable memory including instructions that, when performed by the device, can cause the device to perform acts), such as can include or use a first end portion, the first end portion including a first lumen port, the first lumen port configured to provide access to a first lumen, the first lumen port including a first protrusion extending outwardly therefrom, the first protrusion configured to engage the first lumen, the first end portion including a first plurality of male or female electrical connection features, the first plurality of male or female electrical connection features (1) configured to connect to a first plurality of mating female or male electrical connection features, (2) configured to electrically couple to engage a mating female or male electrical connection feature of a flex circuit ribbon of a catheter, (3) configured to be electrically connected to a male or female electrical connection feature of a second plurality of male or female electrical connection features, and (4) (i) circularly evenly distributed about the first lumen port and extending radially outward from the first lumen port or (ii) configured to permanently engage a female or male connection feature of the flex circuit ribbon and linearly evenly distributed. Example 40 can optionally include or use a second end portion, the second end portion including a second lumen port, the second lumen port configured to provide access to a second lumen, the second lumen port including a second protrusion extending outwardly therefrom, the second protrusion configured to engage the second lumen, the second end portion including the second plurality of male or female electrical connection features, the second plurality of male or female electrical connection features (1) configured to connect to a second plurality of mating female or male electrical connection features, and (2) being circularly evenly distributed about the second lumen port.

Example 41 can include or use, or can be optionally combined with the subject matter of at least one of Examples 1-40, to include subject matter (such as an apparatus, a method, a means for performing acts, or a device readable memory including instructions that, when performed by the device, can cause the device to perform acts), such as can include or use a first end portion, configured to connect to a first connector or a second end portion, configured to connect to a second connector. Example 41 can optionally include or use a lumen port, configured to provide access to (1) a first lumen near the first end portion and (2) a second lumen near the second end portion. Example 41 can optionally include or use a first plurality of male or female electrical connection features, the first plurality of male or female electrical connection feature configured to electrically couple to a first conductor near the first end portion or a second plurality of male or female electrical connection features, the second plurality of male or female electrical connection features configured to electrically couple to a second conductor near the second end portion.

Example 42 can include or use, or can optionally be combined with the subject matter of at least one of Examples 1-41, to optionally include or use the first end portion of the interface connector wherein the first end portion of the interface connector can be configured to couple to the proximal end portion of a catheter. Example 42 can optionally include or use the first plurality of male or female electrical connection features wherein the first plurality of male or female electrical connection features can be circularly distributed (1) about the lumen port and (2) near the first end portion of the interface connector. Example 42 can optionally include or use the first plurality of male or female electrical connection features wherein the first plurality of male or female electrical connection features can be configured to be electrically connected to at least one male or female electrical connection feature of the second plurality of male or female electrical connection features. Example 42 can optionally include or use the second plurality of male or female electrical connection features wherein the second plurality of male or female electrical connection features can be linearly distributed near the second end portion of the interface connector.

Example 43 can include or use, or can optionally be combined with the subject matter of at least one of Examples 1-42, to optionally include or use the second plurality of male or female electrical connection features wherein the second plurality of male or female electrical connection features can be configured to electrically couple to a multi-row connector.

Example 44 can include or use, or can optionally be combined with the subject matter of at least one of Examples 1-43, to optionally include or use the first end portion of the interface connector wherein the first end portion of interface connector can be configured to electrically and mechanically couple to an electrically conductive elongated tubular member.

Example 45 can include or use, or can optionally be combined with the subject matter of at least one of Examples 1-44, to optionally include or use the first plurality of male or female electrical connection features wherein the first plurality of male or female electrical connection features can be circularly distributed about the lumen port near the first end portion of the interface connector.

Example 46 can include or use, or can optionally be combined with the subject matter of at least one of Examples 1-45, to optionally include or use the first plurality of male or female electrical connection features wherein the first plurality of male or female electrical connection features can be configured to be electrically connected to at least one male or female electrical connection feature of the second plurality of male or female electrical connection features.

Example 47 can include or use, or can optionally be combined with the subject matter of at least one of Examples 1-46, to optionally include or use the second plurality of male or female electrical connection features wherein the second plurality of male or female electrical connection features can be linearly distributed near the second end portion of the interface connector.

Example 48 can include or use, or can optionally be combined with the subject matter of at least one of Examples 1-47, to optionally include or use the lumen port wherein the lumen port can be configured to engage the first or second lumen.

Example 49 can include or use, or can optionally be combined with the subject matter of at least one of Examples 1-48, to optionally include or use the lumen port wherein the lumen port can include one or more protrusions extending outwardly from the lumen port near the first or second end portion of the interface connector to engage the first or second lumen.

Example 50 can include or use, or can optionally be combined with the subject matter of at least one of Examples 1-49, to optionally include or use a protrusion at least partially around the perimeter of the first or second end portion of the interface connector, the protrusion configured to surround at least a portion of the first or second connector, and the protrusion configured to increase the strength of a mechanical connection between the interface connector and at least one of the first or second connectors.

Example 51 can include or use, or can be optionally combined with the subject matter of at least one of Examples 1-50, to include subject matter (such as an apparatus, a method, a means for performing acts, or a device readable memory including instructions that, when performed by the device, can cause the device to perform acts), such as can include or use an interface connector configured to (1) connect to a first connector at or near a first end portion of the interface connector and (2) connect to a second connector at or near a second end portion of the interface connector, the method including providing access, using a lumen port, to a first lumen at or near the first end portion, or providing access, using the lumen port, to a second lumen at or near the second end portion. Example 51 can optionally include or use electrically connecting, at or near the first end portion, a first male or female electrical connection feature to a first conductor, or electrically connecting, at or near the second end portion, a second male or female electrical connection feature to a second conductor.

Example 52 can include or use, or can optionally be combined with the subject matter of at least one of Examples 1-51, to optionally include or use electrically and mechanically coupling the first end portion to the proximal end portion of an at least partially implantable biocompatible catheter.

Example 53 can include or use, or can optionally be combined with the subject matter of at least one of Examples 1-52, to optionally include or use electrically coupling the second plurality of male or female electrical connection features to a multi-row connector.

Example 54 can include or use, or can optionally be combined with the subject matter of at least one of Examples 1-53, to optionally include or use electrically connecting the interface connector to an electrically conductive elongated tubular member.

Example 55 can include or use, or can optionally be combined with the subject matter of at least one of Examples 1-54, to optionally include or use electrically connecting the first plurality of male or female electrical connection features circularly distributed about the lumen port at or near the first end portion of the interface connector to a mating female or male electrical connection feature.

Example 56 can include or use, or can optionally be combined with the subject matter of at least one of Examples 1-55, to optionally include or use electrically connecting the second plurality of male or female electrical connection features linearly evenly distributed at or near the second end portion of the interface connector.

Example 57 can include or use, or can optionally be combined with the subject matter of at least one of Examples 1-56, to optionally include or use engaging the first or second lumen.

Example 58 can include or use, or can optionally be combined with the subject matter of at least one of Examples 1-57, to optionally include or use engaging the first or second lumen wherein engaging the first or second lumen can include engaging the first or second lumen with protrusions extending outwardly from the lumen port at or near the first or second end portion of the interface connector.

Example 59 can include or use, or can optionally be combined with the subject matter of at least one of Examples 1-58, to optionally include or use surrounding at least a portion of the first or second connector with a protrusion around the perimeter of the first or second end portion of the interface connector, to increase the strength of the connection between the interface connector and at least one of the first or second connectors.

Example 60 can include or use, or can be optionally combined with the subject matter of at least one of Examples 1-59, to include subject matter (such as an apparatus, a method, a means for performing acts, or a device readable memory including instructions that, when performed by the device, can cause the device to perform acts), such as can include or use a first end portion, (1) configured to connect to a first connector, (2) configured to electrically and mechanically couple to a proximal end portion of a tubular catheter that includes an electrical conductor or a second end portion, configured to connect to a second connector. Example 60 can optionally include or use a lumen port, configured to provide access to (1) a first lumen at or near the first end portion and (2) a second lumen at or near the second end portion, the lumen port including a protrusion extending outwardly from the lumen port at or near the first or second end portion of the interface connector to engage the first or second lumen. Example 60 can optionally include or use a first plurality of male or female electrical connection features being (1) configured to electrically couple to a first conductor near the first end portion, (2) circularly evenly distributed (i) about the lumen port and (ii) at or near the first end portion of the interface connector, (3) configured to be respectively electrically connected to at least one male or female electrical connection feature of a second plurality of male or female electrical connection features. Example 60 can optionally include or use the second plurality of male or female electrical connection features, the second plurality of male or female electrical connection features can be (1) configured to electrically couple to a second conductor at or near the second end portion, (2) linearly evenly distributed at or near the second end portion of the interface connector, (3) configured to electrically couple to a multi-row connector. Example 60 can optionally include or use a protrusion at least partially around the perimeter of the first or second end portion of the interface connector, the protrusion configured to surround at least a portion of the first or second connector, and the protrusion configured to increase the strength of a mechanical connection between the interface connector and the first or second connector.

Example 61 can include or use, or can optionally be combined with the subject matter of at least one of Examples 1-60, to optionally include or use an end-user attachable or detachable elongated interchangeable distal portion of a catheter including a connector portion, configured to electrically and mechanically couple to an elongated less distal portion of the catheter that includes an electrical conductor, the connector portion configured to allow an end-user to selectively attach the interchangeable distal portion to or selectively detach the interchangeable distal portion from the elongated less distal portion of the catheter such that when the interchangeable distal portion is attached to the elongated less distal portion of the catheter the interchangeable distal portion can be the most distal portion of the catheter.

Example 62 can include or use, or can optionally be combined with the subject matter of at least one of Examples 1-61, to optionally include or use the connector portion configured to electrically couple to and be laterally flush with a mating connector portion of the elongated less distal portion of the catheter, the connector portion including a first gasket configured to seal a coupling and configured to (1) allow a conductor to pass through the first gasket and (2) to provide access to a lumen of the interchangeable distal portion or of the elongated less distal portion of the catheter.

Example 63 can include or use, or can optionally be combined with the subject matter of at least one of Examples 1-62, to optionally include or use the connector portion wherein the connector portion can be configured to provide a second gasket at a proximal interface of the interchangeable distal portion.

Example 64 can include or use, or can optionally be combined with the subject matter of at least one of Examples 1-63, to optionally include or use the connector portion wherein the connector portion can be configured to provide a third gasket at a proximal interface of the interchangeable distal portion.

Example 65 can include or use, or can optionally be combined with the subject matter of at least one of Examples 1-64, to optionally include or use a proximal end of the interchangeable distal portion wherein the proximal end of the interchangeable distal portion includes a stepped profile.

Example 66 can include or use, or can optionally be combined with the subject matter of at least one of Examples 1-65, to optionally include or use a Josephson, Cournand, conduction study, multipurpose, D'Amato, or K-curve shape.

Example 67 can include or use, or can optionally be combined with the subject matter of at least one of Examples 1-66, to optionally include or use an elongated inner portion, an elongated outer portion, or at least one conductor, the at least one conductor disposed between (1) the inner portion and (2) the outer portion, wherein the inner portion and the outer portion can be integrally formed or affixed together between portions of the at least one conductor. Example 67 can optionally include or use an electrical contact, configured to be exposed during use, the electrical contact connected to the at least one conductor.

Example 68 can include or use, or can optionally be combined with the subject matter of at least one of Examples 1-67, to optionally include or use the interchangeable distal portion wherein the interchangeable distal portion can be a portion of an at least partially implantable biocompatible catheter, the interchangeable tip including the elongated inner portion, the elongated outer portion, the at least one conductor, and the electrical contact, wherein the electrical contact can include an electrode, the elongated inner portion can include an elongated inner member including an outer surface, the elongated outer portion can include an elongated tubular outer member including an inner surface. Example 68 can optionally include or use the at least one conductor wherein the at least one conductor can be disposed between (1) the outer surface of the elongated inner member and (2) the inner surface of the elongated outer tubular member, the at least one conductor is helically wound about the elongated inner member. Example 68 can optionally include or use the elongated inner member and the elongated tubular outer member wherein the elongated inner member and the elongated tubular outer member can be bonded helically together between helically wound portions of the at least one conductor.

Example 69 can include or use, or can optionally be combined with the subject matter of at least one of Examples 1-68, to optionally include or use a flex circuit ribbon including the at least one conductor or a stiffener selectively situated on a surface of the flex circuit ribbon.

Example 70 can include or use, or can optionally be combined with the subject matter of at least one of Examples 1-69, to optionally include or use a greater quantity of the stiffener wherein a greater quantity of the stiffener can be situated on a first portion of the surface of the flex circuit ribbon than on a longitudinally different second portion of the surface of the flex circuit ribbon.

Example 71 can include or use, or can be optionally be combined with the subject matter of at least one of Examples 1-70, to include subject matter (such as an apparatus, a method, a means for performing acts, or a device readable memory including instructions that, when performed by the device, can cause the device to perform acts), such as can include or use making an end-user attachable or detachable elongated interchangeable distal portion of a catheter including configuring a connector portion of the interchangeable distal portion to electrically and mechanically couple to an elongated less distal portion of the catheter that includes an electrical conductor. Example 71 can optionally include or use configuring the connector portion to allow an end-user to selectively attach the interchangeable distal portion to or selectively detach the interchangeable distal portion from the elongated less distal portion of the catheter such that when the interchangeable distal portion is attached to the elongated less distal portion of the catheter the interchangeable distal portion can be the most distal portion of the catheter.

Example 72 can include or use, or can optionally be combined with the subject matter of at least one of Examples 1-71, to optionally include or use configuring the connector portion of the interchangeable distal portion to seal a coupling with the elongated less distal portion of the catheter while passing an electrical conductor and providing access to a lumen of the interchangeable distal portion or the elongated less distal portion.

Example 73 can include or use, or can optionally be combined with the subject matter of at least one of Examples 1-72, to optionally include or use configuring the connector portion of the interchangeable distal portion to include first and second gaskets.

Example 74 can include or use, or can optionally be combined with the subject matter of at least one of Examples 1-73, to optionally include or use configuring the connector portion with a stepped profile for aligning and mating with a corresponding profile of the elongated less distal portion of the catheter.

Example 75 can include or use, or can optionally be combined with the subject matter of at least one of Examples 1-74, to optionally include or use providing the interchangeable distal portion to include a Josephson, Cournand, conduction study, multipurpose, D'Amato, or K-curve shape.

Example 76 can include or use, or can optionally be combined with the subject matter of at least one of Examples 1-75, to optionally include or use configuring the interchangeable distal portion to be capable of laterally flush connection with the elongated less distal portion of the catheter.

Example 77 can include or use, or can optionally be combined with the subject matter of at least one of Examples 1-76, to optionally include or use situating at least one conductor between (1) an elongated inner portion of the interchangeable distal portion and (2) an elongated outer portion of the interchangeable distal portion. Example 77 can optionally include or use (1) affixing the elongated inner portion and the elongated outer portion together between portions of the at least one conductor or (2) integrally forming the elongated inner portion and elongated outer portion. Example 77 can optionally include or use connecting an electrical contact, configured to be exposed during use, to the at least one conductor.

Example 78 can include or use, or can optionally be combined with the subject matter of at least one of Examples 1-77, to optionally include or use the at least conductor wherein the at least one conductor can be included in a flex circuit ribbon, and including making an at least partially implantable biocompatible end-user attachable or detachable elongated interchangeable distal portion of a catheter, the interchangeable distal portion configured to allow an end-user to attach the interchangeable distal portion to and to allow an end-user to detach the interchangeable distal portion from an at least partially implantable biocompatible electrically conductive elongated member. Example 78 can optionally include or use situating the flex circuit ribbon can include disposing the flex circuit ribbon between (1) an outer surface of an elongated inner member of the elongated inner portion and (2) an inner surface of an elongated tubular outer member of the elongated outer portion. Example 78 can optionally include or use situating the flex circuit ribbon including winding the flex circuit ribbon helically about the elongated inner member. Example 78 can optionally include or use affixing the elongated inner portion and the elongated outer portion can include helically bonding the elongated inner member and the elongated outer member together between helically wound portions of the flex circuit ribbon.

Example 79 can include or use, or can optionally be combined with the subject matter of at least one of Examples 1-78, to optionally include or use selectively situating a stiffener on a surface of the flex circuit ribbon.

Example 80 can include or use, or can be optionally combined with the subject matter of at least one of Examples 1-79, to include subject matter (such as an apparatus, a method, a means for performing acts, or a device readable memory including instructions that, when performed by the device, can cause the device to perform acts), such as can include or use an at least partially implantable biocompatible end-user attachable or detachable elongated interchangeable distal portion of a catheter including an electrode, an elongated inner member including an outer surface, or an elongated tubular outer member including an inner surface. Example 80 can optionally include or use a flex circuit ribbon including at least one conductor disposed between (1) the outer surface of the elongated inner member and (2) the inner surface of the elongated outer tubular member, the at least one conductor helically wound about the elongated inner member. Example 80 can optionally include or use the elongated inner member and the elongated tubular outer member bonded helically together between helically wound portions of the at least one conductor, a stiffener selectively situated on a surface of the flex circuit ribbon, a stepped profile at a proximal end of the interchangeable distal portion, or a Josephson, Cournand, conduction study, multipurpose, D'Amato, or K-curve shape. Example 80 can optionally include or use a connector portion, configured to (1) electrically and mechanically couple to an elongated less distal portion of the catheter that includes an electrical conductor, (2) allow an end-user to selectively attach the interchangeable distal portion to or selectively detach the interchangeable distal portion from the elongated less distal portion of the catheter such that when the interchangeable distal portion is attached to the elongated less distal portion of the catheter the interchangeable distal portion can be the most distal portion of the catheter, (3) electrically couple to and be laterally flush with a mating connector portion of the elongated less distal portion of the catheter, the connector portion including a first gasket configured to seal a coupling and configured to (1) allow a conductor to pass through the first gasket and (2) to provide access to a lumen of the interchangeable distal portion or of the elongated less distal portion of the catheter, and second and third gaskets at a proximal interface of the interchangeable distal portion.

The above detailed description comprises references to the accompanying drawings, which form a part of the detailed description. The drawings show, by way of illustration, specific embodiments in which the invention can be practiced. These embodiments are also referred to herein as "examples." Such examples can comprise elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In this document, the terms "a" or "an" are used, as is common in patent documents, to comprise one or more than one, independent of any other instances or usages of "at least one" or "one or more." In this document, the term "or" is used to refer to a nonexclusive or, such that "A or B" comprises "A but not B," "B but not A," and "A and B," unless otherwise indicated. In this document, the terms "comprising" and "in which" are used as the plain-English equivalents of the respective terms "comprising" and "wherein." Also, in the following claims, the terms "comprising" and "comprising" are open-ended, that is, a system, device, article, composition, formulation, or process that comprises elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can comprise a computer-readable medium or machine-readable medium encoded with instructions operable to configure an electronic device to perform methods as described in the above examples. An implementation of such methods can comprise code, such as microcode, assembly language code, a higher-level language code, or the like. Such code can comprise computer readable instructions for performing various methods. The code can form portions of computer program products. Further, in an example, the code can be tangibly stored on one or more volatile, non-transitory, or non-volatile tangible computer-readable media, such as during execution or at other times. Examples of these tangible computer-readable media can comprise, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) can be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features can be grouped together to streamline the disclosure. This should not be interpreted as intending that an unclaimed disclosed feature is essential to any claim. Rather, inventive subject matter can lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. An apparatus, comprising:
an elongated inner portion;
an elongated outer portion;
a flex circuit ribbon, comprising at least one conductor embedded in a flexible insulator, the flex circuit ribbon situated between the inner portion and the outer portion, wherein the inner portion and the outer portion are bonded together between wound portions of the flex circuit ribbon;
an electrical contact included in or connected to the at least one conductor of the flex circuit ribbon; and
a connector configured to connect an end-user attachable or detachable elongated portion to the flex circuit ribbon, the connector comprising a first plurality of electrical connectors configured to be respectively individually coupled to the conductors of the flex circuit ribbon.

2. The apparatus of claim 1, comprising an at least partially implantable biocompatible catheter comprising the inner portion, the outer portion, the flex circuit ribbon, the electrical contact, and the connector, wherein:
the electrical contact comprises an electrode;
the inner portion comprises an elongated inner member comprising an outer surface;
the outer portion comprises an elongated tubular outer member comprising an inner surface; and
the flex circuit ribbon is situated between (1) the outer surface of the inner member and (2) the inner surface of the outer member, and the flex circuit ribbon is helically wound about the inner member.

3. The apparatus of claim 1, wherein the first plurality of electrical connectors are configured to permanently engage a conductor of the plurality of conductors of the flex circuit ribbon.

4. The apparatus of claim 1, wherein the first plurality of electrical connectors are evenly spaced about a lumen port of the connector that provides access to a lumen of the elongated inner portion.

5. The apparatus of claim 1, wherein the first plurality of electrical connectors longitudinally extend outward in a radial pattern about a longitudinal axis of the inner portion.

6. The apparatus of claim 1, further comprising an end-user attachable or detachable elongated portion comprising a second connector configured to permit an end-user to (1) electrically couple the end-user attachable or detachable elongated portion to or (2) electrically decouple the end-user attachable or detachable elongated portion from the first plurality of electrical connectors.

7. The apparatus of claim 6, wherein the connector includes a first lumen port that provides access to a lumen of the elongated inner portion and the second connector comprises a second plurality of electrical connectors and a second lumen port accessible through the first lumen port, the second plurality of electrical connectors configured to individually respectively electrically couple with the first plurality of electrical connectors and distributed about the second lumen port.

8. The apparatus of claim 7, wherein the second plurality of electrical connectors are evenly spaced about the second lumen port.

9. The apparatus of claim 6, wherein the connector includes a first lumen port that provides access to a lumen of the elongated inner portion and the second connector comprises protrusions situated peripherally about a second lumen port of the second connector, the protrusions configured to engage the lumen.

10. The apparatus of claim 1, comprising a stiffener selectively situated on a surface of the flex circuit ribbon.

11. The apparatus of claim 10, wherein the stiffener is a conductive material including stainless steel, copper, aluminum, Cupernickel, nitinol, Inconel, platinum, or a combination thereof.

12. The apparatus of claim 11, wherein the conductive material includes a shape-memory material that returns to a specified shape when heated to a sufficient temperature.

13. The apparatus of claim 10, wherein the stiffener is situated on a first portion of the surface of the flex circuit ribbon and a second portion of the surface of the flex circuit ribbon and a greater quantity of the stiffener is situated on the first portion of the surface of the flex circuit ribbon than on the second portion of the surface of the flex circuit ribbon, wherein the first portion of the surface of the flex circuit ribbon is longitudinally situated differently on the apparatus than the second portion of the surface of the flex circuit ribbon, wherein the stiffener on the first portion of the flex circuit ribbon includes a first patch of material physically separate from a second patch of material on the second portion of the flex circuit ribbon.

14. The apparatus of claim 1, wherein the flex circuit ribbon includes an electrical connection feature in a portion of the flex circuit ribbon situated about the connector and the electrical connection feature is configured to engage the first plurality of electrical connectors.

15. A method of making an apparatus, the method comprising: situating a flex circuit ribbon, comprising a plurality of conductors embedded in a flexible insulator, between an elongated inner portion and an elongated outer portion by winding the flex circuit ribbon about the elongated inner portion; bonding the inner portion and the outer portion together between wound portions of the flex circuit ribbon; and electrically coupling a first connector to the flex circuit ribbon by respectively individually electrically coupling a first plurality of electrical connectors of the first connector to the plurality of conductors of the flex circuit ribbon.

16. The method of claim 15, further comprising selectively situating a stiffener on a surface of the flex circuit ribbon in at least a first portion and a second portion of the flex circuit ribbon, the first portion longitudinally situated differently along the flex circuit ribbon than the second portion of the flex circuit ribbon, wherein a greater quantity of the stiffener is situated on the first portion of the flex circuit ribbon than on a second portion of the surface of the flex circuit ribbon.

17. The method of claim 16, wherein selectively situating the stiffener includes situating the stiffener on the surface of the flex circuit ribbon and etching the stiffener to remove at least a portion of the stiffener.

18. The method of claim 15, further comprising electrically coupling an end-user attachable or detachable elongated portion to or electrically de-coupling the end-user attachable or detachable elongated portion from the first connector.

19. The method of claim 18, where electrically coupling the end-user attachable or detachable elongated portion to or electrically de-coupling the end-user attachable or detachable elongated portion from the connector includes electrically coupling a second plurality of electrical connectors situated about a lumen port of the end-user attachable or detachable elongated portion to the first plurality of electrical connectors of the first connector.

20. An apparatus comprising: a biocompatible catheter comprising: an elongated inner portion, comprising an elongated tubular inner member comprising an outer surface; an elongated outer portion, comprising an elongated tubular outer member comprising an inner surface; a flex circuit ribbon, comprising at least one conductor embedded in a flexible insulator, the flex circuit ribbon disposed between (1) the outer surface of the elongated tubular inner member and (2) the inner surface of the elongated tubular outer member, the flex circuit ribbon wound about the elongated tubular inner member, wherein the inner portion and the outer portion are bonded together between wound portions of the flex circuit ribbon; an electrical contact included in or connected to the at least one conductor of the flex circuit ribbon, the electrical contact comprising a plurality of discrete electrodes situated about the flex circuit ribbon so as to provide a specified electric field distribution for the apparatus; a stiffener selectively situated on a first portion and a second portion of the surface of the flex circuit ribbon to provide a specified stiffener pattern on the surface of the flex circuit ribbon, wherein a greater quantity of the stiffener is situated on the first portion of the surface of the flex circuit ribbon than on the second portion of the surface of the flex circuit ribbon, wherein the first portion of the surface of the flex circuit ribbon is longitudinally situated differently on the apparatus than the second portion of the surface of the flex circuit ribbon; a connector configured to be electrically coupled to the flex circuit ribbon, the connector comprising a plurality of electrical connectors configured to be respectively individually coupled to conductors of the flex circuit ribbon; and an end-user attachable or end-user detachable elongated portion configured to permit an end-user to (1) electrically couple the end-user attachable or detachable elongated portion to or (2) electrically decouple the end-user attachable or detachable elongated portion from the connector.

* * * * *